United States Patent
Ueda et al.

(10) Patent No.: US 9,207,215 B2
(45) Date of Patent: *Dec. 8, 2015

(54) METHOD FOR EVALUATING HIT FEELING

(75) Inventors: Naoyoshi Ueda, Kobe (JP); Masahiko Ueda, Kobe (JP); Takeshi Asakura, Kobe (JP)

(73) Assignees: DUNLOP SPORTS CO. LTD, Kobe-shi (JP); SUMITOMO RUBBER INDUSTRIES, LTD., Kobe-shi (JP)

( * ) Notice: Subject to any disclaimer, the term of this patent is extended or adjusted under 35 U.S.C. 154(b) by 740 days.

This patent is subject to a terminal disclaimer.

(21) Appl. No.: 13/455,368

(22) Filed: Apr. 25, 2012

(65) Prior Publication Data
US 2012/0277035 A1 Nov. 1, 2012

(30) Foreign Application Priority Data
Apr. 26, 2011 (JP) ................................. 2011-098104

(51) Int. Cl.
*G01N 29/04* (2006.01)
*G01L 5/00* (2006.01)
*G01N 29/14* (2006.01)
*G01N 3/30* (2006.01)

(52) U.S. Cl.
CPC ............ *G01N 29/045* (2013.01); *G01L 5/0052* (2013.01); *G01N 29/14* (2013.01); *G01N 3/30* (2013.01); *G01N 2203/0658* (2013.01)

(58) Field of Classification Search
CPC .... A63B 57/00; A63B 59/0074; A63B 53/00; A63B 53/04; A63B 2053/005; A63B 37/0003; G01N 29/045; G01N 29/14; G01N 3/30; G01N 2203/0658; G01L 5/0052
USPC ............................................ 73/120; 473/409
See application file for complete search history.

(56) References Cited

U.S. PATENT DOCUMENTS

| | | | | |
|---|---|---|---|---|
| 5,056,783 A * | 10/1991 | Matcovich et al. | ........... | 473/453 |
| 6,705,952 B1 * | 3/2004 | Vecsey | .............. | 473/232 |
| 2007/0287552 A1 * | 12/2007 | Sugimoto | .................... | 473/345 |
| 2008/0115582 A1 | 5/2008 | Sato et al. | | |
| 2009/0143159 A1 * | 6/2009 | Murph et al. | ................ | 473/239 |
| 2009/0309172 A1 * | 12/2009 | Liu et al. | ....................... | 257/415 |
| 2010/0304877 A1 * | 12/2010 | Iwahashi et al. | ............. | 473/223 |
| 2011/0067507 A1 * | 3/2011 | Miyamae | .................... | 73/865.9 |
| 2011/0077095 A1 * | 3/2011 | Olsson et al. | ................ | 473/287 |
| 2011/0111872 A1 * | 5/2011 | Ishii | ............................ | 473/219 |
| 2011/0124440 A1 * | 5/2011 | Ueda et al. | .................... | 473/409 |
| 2011/0165960 A1 * | 7/2011 | Slaughter | ..................... | 473/309 |
| 2011/0230986 A1 * | 9/2011 | Lafortune et al. | ............. | 700/93 |

FOREIGN PATENT DOCUMENTS

JP 2002-286565 A 10/2002

* cited by examiner

*Primary Examiner* — Lisa Caputo
*Assistant Examiner* — Philip Cotey
(74) *Attorney, Agent, or Firm* — Birch, Stewart, Kolasch & Birch, LLP

(57) ABSTRACT

The evaluation method includes a first step, by using measurement means M1 which can measure force F acting between a swing subject and the sport hitting tool or a specific directional component F1 thereof, obtaining measured value Vf of the force F or the force F1 at time after the impact, and a second step of determining the hit feeling on the basis of the measured value Vf at least at the one time. Preferably, the force F or the force F1 is force Fs containing a component in a shear direction. Preferably, in the first step, the measured values Vf in a specific interval Z 12 from time T1 to T2 after the impact are obtained chronologically. Preferably, the evaluation is made based on a difference between a maximum value and a minimum value of the measured values Vf.

13 Claims, 28 Drawing Sheets

METHOD FOR EVALUATING HIT FEELING

This application involves a claim for benefits based on Japanese Patent Application No. 2011-98104 filed on Apr. 26, 2011, which is incorporated herein in its entirety by reference.

BACKGROUND OF THE INVENTION

1. Field of the Invention

The present invention relates to a method for evaluating hit feeling with sport hitting tools.

2. Description of the Related Art

A number sport hitting tools such as a golf club, a tennis racket, a badminton racket, a table tennis racket, a baseball bat and the like are used.

There exists hit feeling in these sport hitting tools. In the case of sport hitting a ball, hit feeling is also referred to as hitting ball feeling. The hit feeling is an important element for selecting a sport hitting tool. The hit feeling indicates compatibility of a sport hitting tool with its user. The hit feeling tends to correlate with a result. A good result tends to be obtained with a sport hitting tool with good hit feeling. The hit feeling is an extremely important factor as the properties of sport hitting tools.

Japanese Patent Application Publication No. 2002-286565 discloses a method for measuring impact force. The impact force may correlate with hit feeling. Japanese Patent Application Publication No. 2006-125722 (US2008/0115582) discloses a method for evaluating hit feeling by measuring vibration in a circumferential direction of a shaft.

SUMMARY OF THE INVENTION

The hit feeling is a sense of a human body. Evaluation of hit feeling is difficult. Impact force is force acting on a golf club, and vibration of a shaft is behavior of the golf club itself. The impact force and the shaft behavior are information far from a human (player). The inventor believed that evaluation of the hit feeling sensed by the human being requires measurement of near information from the human being (player). Consequently, the inventor found a method for evaluating hit feeling with higher reliability.

An object of the present invention to provide a new evaluation method which enables quantification of hit feeling.

The evaluation method of the present invention is a method for quantitatively evaluating hit feeling of sport hitting tools. The method includes a first step, by using measurement means M1 which can measure force F acting between a swing subject and the sport hitting tool or a specific directional component F1 thereof, obtaining measured value Vf of the force F or the force F1 at time after the impact, and a second step of determining the hit feeling on the basis of the measured value Vf at least at the one time.

Preferably, the force F or the force F1 is force is containing a component in a shear direction. The swing subject may be a swing robot.

Preferably, in the first step, the measured values Vf in a specific Interval Z12 from time T1 to time T2 after the impact are obtained chronologically. Preferably, in the second step, the hit feeling is evaluated based on an integrated value if of the measured values Vf in the specific interval Z12.

Preferably, in the first step, the measured values Vf in the specific interval Z12 from the time T1 to the time T2 after the impact are obtained chronologically. Preferably, in the second step, the hit feeling is evaluated based on a change rate Rd of the measured values Vf in the specific interval Z12.

Preferably, in the first step, the measured values Vf in the specific interval Z12 from the time T1 to the time T2 after the impact are obtained chronologically. Preferably, in the second step, the hit feeling is evaluated based on a difference between a maximum value and a minimum value of the measured values Vf in the specific interval Z12.

Preferably, the time T1 is impact time Tp. Preferably, the specific interval Z12 is equal to or less than 100 msec. The time T1 may be time Tmin when the measured value Vf reaches the minimum in a predetermined interval.

If time when the measured value Vf reach the maximum between the impact time Tp and time after a lapse of 50 msec from the time Tp is defined as Tmax, preferably, the time Tmin is time when the measured value Vf reaches the minimum between the impact time Tp and the time Tmax.

Preferably, in the first step, measurement data is sorted by considering uniformity of a swing speed and/or uniformity of hit points.

Preferably, the measurement means M1 includes a force sensor provided in at least one of the swing subject or the sport hitting tool. Preferably, a measurement region by the force sensor is determined based on a comparison of a distribution of the measured values Vf in practice swinging and a distribution of the measured values Vf in actual hitting.

Preferably, the force sensor is a three-axis force sensor.

A preferred evaluation method further includes a selection step of selecting a measurement region. Preferably, in the selection step, a pressure sensor provided in at least one of the swing subject or the sport hitting tool is used. Preferably, in the selection step, the measurement region is selected based on a comparison of a distribution on of measured values in practice swinging with the pressure sensor and a distribution of measured values in actual hitting with the pressure sensor. Preferably, in the first step, the force F or the specific directional component F1 of the force F is measured in the measurement region selected in the selection step. Preferably, in the first step, the force F or the specific directional component F1 is measured by a three-axis force sensor.

In the evaluation method according to the present invention, the hit feeling can be quantitatively evaluated.

DESCRIPTION OF THE PREFERRED EMBODIMENTS

Figure 1:
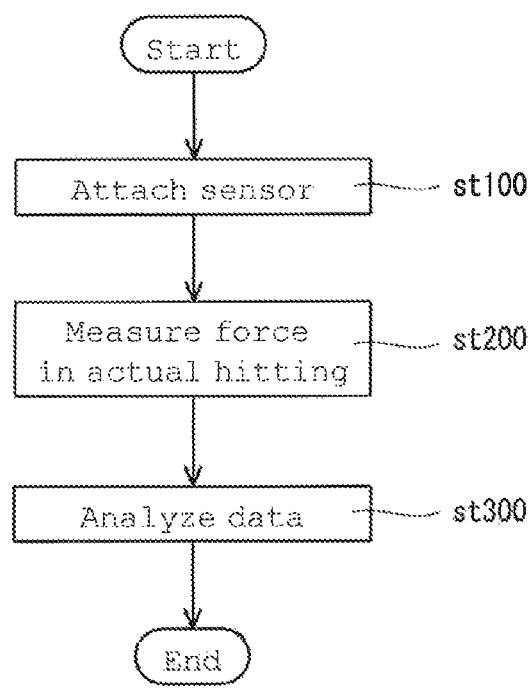
FIG. 1 is a flow chart for illustrating a procedure of an evaluation method according to one embodiment of the present invention.

The present invention will be described in detail on the basis of preferred embodiments, with reference to the drawings, as appropriate.

The present invention is not to measure behavior of a sport hitting tool. This invention is not to measure impact force received due to a hit ball.

In the present invention, force F acting between a swing subject and a sport hitting tool or a specific directional component thereof F1 is measured. A "specific direction" is not limited. The force F or the specific directional component F1 is herein collectively referred to by a term "grip force". The "grip force" is herein simply referred to as "force".

In a first preferred embodiment, force Fs acting between a swing subject and a sport hitting tool are measured. The force Fs contains a component in a shear direction. The shear direction is an x axis direction or a y axis direction to be described hereinafter. One example of the force Fs is actual force F acting between the swing subject and the sport hitting tool. Other example of the force Fs is a specific directional component F1 of the force F. As far as it contains the component in the shear direction, the "specific direction" is not limited.

In a second preferred embodiment, force Fr acting between a swing robot and a sport hitting tool is measured. A direction of the force Fr is not limited. The force Fr may or may not contain a component in a shear direction. One example of the force Fr is the force F mentioned above. Other example of the force Fr is the specific directional component F1 of the force F.

It was learned that there exists a correlation between the force F or the specific directional component F1 and hit feeling. It was also learned that there exists a correlation between the force Fs or the force Fr and the hit feeling. Details thereof will be described hereinafter.

To measure the force Fs or the force Fr, measurement means M1 having a sensor is used. The sensor is provided in at least one of a sport hitting tool or a swing subject.

A sport hitting tool is not limited, and includes a golf club, a tennis racket, a badminton racket, a table tennis racket, a baseball bat, a cricket bat, and a gate ball stick. In the following, a description will be given with a golf club as an example.

A swing subject includes a person or a swing robot. Since hit feeling is to be sensed by a person, the swing subject shall be a person from this standpoint. However, there are some cases in which a swing robot is effective. For example, if there is universal hit feeling common to a number of people, a swing robot is effective in evaluating the hit feeling of a sport hitting tool. As the swing robot has little variation in each swing, it is effective for capturing the universal hit feeling. In the following, cases in which a swing subject is a person will be mainly described. In the present invention, the hit feeling can be quantified. Thus, use of a swing robot can be made possible, although hit feeling is evaluated.

Figure 2:
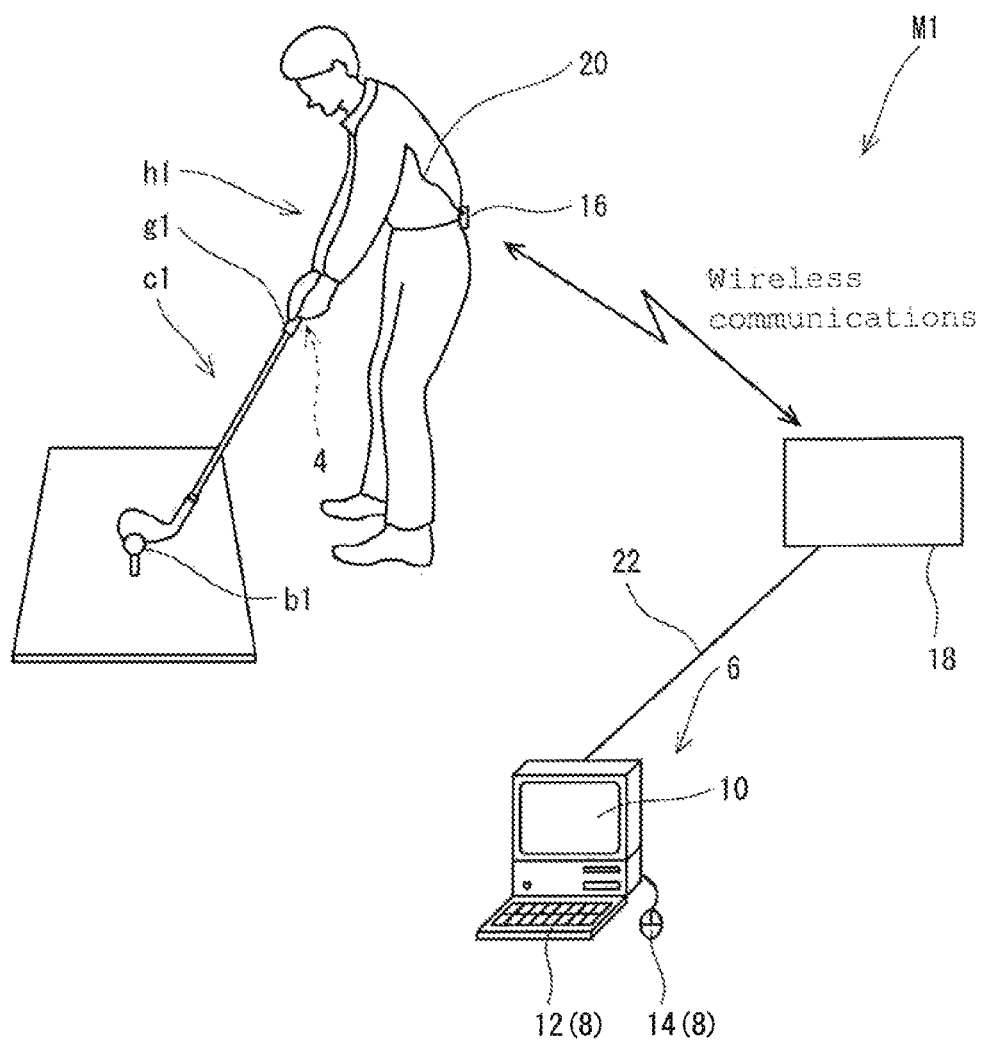
FIG. 2 is a view showing how the evaluation method according to the one embodiment of the present invention is performed.

FIG. 1 is a flow chart showing a procedure of measurement according to one embodiment of the present invention. FIG. 2 is a view showing how measurement of the embodiment is performed. In the measurement, measurement means M1 has a sensor, the sensor 4 being attached to a swing subject (step st100). The swing subject h1 of the embodiment is a human body. The swing subject h1 may be a swing robot. The sensor 4 is disposed on a palm of the swing subject h1. More specifically, the sensor 4 is disposed on a palm portion of a glove worn by the swing subject h1. Alternatively, the sensor 4 may be provided directly on the skin of the human body. In addition, the sensor may be provided on a sport hitting tool c1.

The sensor 4 (not shown) of the embodiment is a pressure sensor. When the swing subject is a person, the sensor is attached to a palm side c1 the person or a grip side of a golf club. In the embodiment, the human body wears a glove to which the sensor is attached. When the swing subject is a swing robot, the sensor 4 is attached between the swing robot and a grip g1. The sensor 4 is attached to a contact surface between the swing subject h1 and the grip g1. One example of a preferred sensor is a sheet-like pressure sensor. The sheet-like sensor does not prevent swinging. A sensor capable of measuring force Fs containing a component in a shear direction may be attached, in place of the pressure sensor. One example of the sensor is a three-axis force sensor to be described hereinafter.

Then, force in actual hitting is measured (step st200). In the application, "actual hitting" means that a ball b1 is hit by swinging. The "actual hitting" and "practice swinging" are contrasting concepts. The "practice swinging" is swinging without hitting a ball b1, while the "actual hitting" is swinging for hitting a ball b1. The actual hitting may be performed by a swing robot or a human body. The practice swinging may be performed by a swing robot or a human body.

Next, data is analyzed (stem st300). The data analysis is performed by an arithmetic processing unit 6. Details of the analysis will be described hereinafter.

The measurement means M1 has a pressure sensor 4 and the arithmetic processing unit 6. The arithmetic processing unit 6 includes a computer. Typically, the arithmetic processing unit 6 includes an operating input section 8, a data input section (not shown), a display section 10, a hard disk (not shown), a memory (not shown), and a CPU (not shown). The operating input section 8 includes a keyboard 12 and a mouse 14.

The data input section includes an interface board for inputting A/D converted digital data, for example. Data inputted in the data input section is outputted to the CPU. The display section 10 is a display, for example. The display section can display various data while being controlled by the CPU.

The CPU reads a program stored in the hard disk, for example, loads it in a working area of the memory, and executes various types of processes according to the program. The memory is a rewritable memory, for example, and configures a storage area or a working area or the like of a program or input data read from the hard disk. The hard disk stores a program, data, and the like, which are necessary for data processing and the like. The program causes the CPU to perform the necessary data processing. One example of the data processing is calculation of an integrated value Sf containing an increased amount Psum to be described hereinafter. Another example of the data processing is calculation of a change rate Rd. Other one example of the data processing is calculation of [Fmax−Fmin] to be described hereinafter.

Data on force is obtained by the sensor 4. The data can be obtained chronologically. For example, force data in a part of or all of times during swinging can be obtained chronologically. For example, chronological (time-series) data is a collection of data to be obtained every certain time. The chronological data enables measurement of any change in force during swinging. The display section 10 can display the chronological data in a graph and the like. The graph of the chronological data will be described hereinafter.

Figure 3:
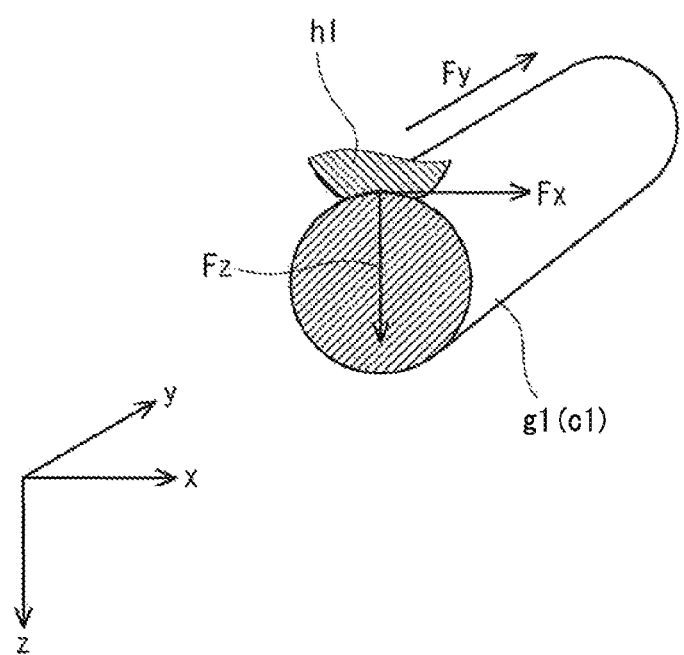
FIG. 3 is a view for illustrating force to be given to a sport hitting tool by a swing subject.

FIG. 3 is a view for illustrating force to be measured in the embodiment. A hatched area designated as a symbol h1 in FIG. 3 is a part of a cross section of a hand of a human body. As shown in FIG. 3, force F to be applied to the sport hitting tool c1 by the swing subject h1 can be decomposed to a component Fx, a component Fy, and a component Fz. In the embodiment, force Fz perpendicularly pressing on the sport hitting tool c1 is measured. The component F1 in the embodiment is the force Fz. The component F1 is not limited and may be the force Fx, the force Fy, or a sum of these vectors. Needless to say, the force F may be measured. In the embodiment, the force Fz is measured by the pressure sensor 4.

Force Fs containing a component in a shear direction may be measured. One example of the force Fs is the force F mentioned above. Other example of the force Fs includes a vector sum of the component Fx and the component Fy. Further other example of the force Fs includes the component Fx and the component Fy. The force Fs is one example of grip force. In addition, when the force Fs is measured, a three-axis force sensor, for example, is used.

The measurement means M1 further has a wireless transmitting device 16 and a wireless receiving device 18. The wireless transmitting device 16 and the sensor 4 are connected by wiring 20. The wireless receiving device 18 and the arithmetic processing unit 6 are connected by wiring 22.

Data measured by the sensor 4 is transmitted to the wireless transmitting device 16. The wireless transmitting device 16 transmits the data. The wireless receiving device 18 receives the data. As a wireless communication method, the standard and technology of Bluetooth, for example, may be preferably used. The wireless receiving device 18 includes a wireless antenna, a wireless interface, a CPU, and a network interface, although they are not shown.

Use of the wireless communications can eliminate the need for wiring which prevents swinging. In this case, a tester t1 as the swing subject h1 can make a original (normal) swing. With the use of the wireless communications, natural swings can be achieved, and thus the measurement accuracy of swings can be improved. In addition, wire communications may be used in place of the wireless communications.

Figure 4:
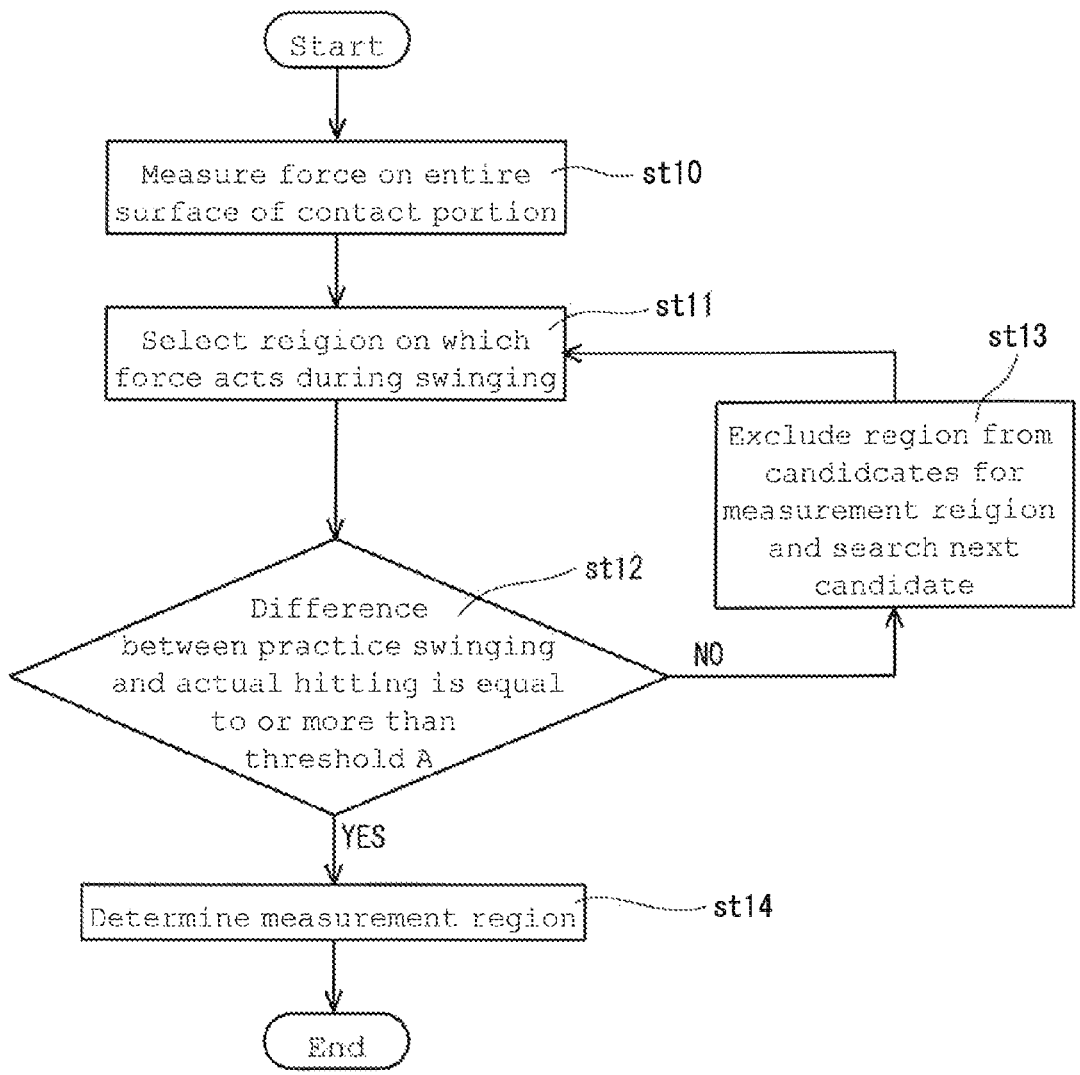
FIG. 4 is a flow chart showing one example of a method for selecting a measurement region, which is a preferred embodiment.

FIG. 4 is a flow chart showing one example of a procedure for determining a position of a sensor. In a preferred embodiment of the present invention, a measurement region is selected prior to attachment of a sensor (step st100 mentioned above).

In a preferred method for selecting a measurement region, force on an entire surface of a contact portion is measured (step st10). Force to be measured includes pressure (Fz mentioned above). Other force to be measured includes the force Fs. In the following, a description will be given of a case in which force to be measured is pressure, as an example. In the step st10, pressure sensors are disposed on all contact faces between a swing subject h1 and a sport hitting tool c1. Then, a region on which force acts during a swing is selected (step st11). In the step st11, force in practice swinging is compared with force in actual hitting. Then, it is determined whether for a certain measurement region, a difference between force in practice swinging and force in actual hitting is equal to or greater than a threshold A (step st12). The threshold A is set, as appropriate, corresponding to the swing subject h1 or the sport hitting tool c1 and the like. In addition, it is preferable that the threshold A is set so that a correlation between a measurement result to be obtained finally and the hit feeling is high.

When the difference between the force in practice swinging and that in the actual hitting is leas than the threshold A, the measurement region is excluded from candidates and other candidate is searched (step st13). Then, for the other candidate, it is judged whether a difference between force in practice swinging and that in actual hitting is equal to or greater than the threshold A (step st12). If the difference is equal to or greater than the threshold A, that region is determined as a measurement region (step st14).

Figure 5:
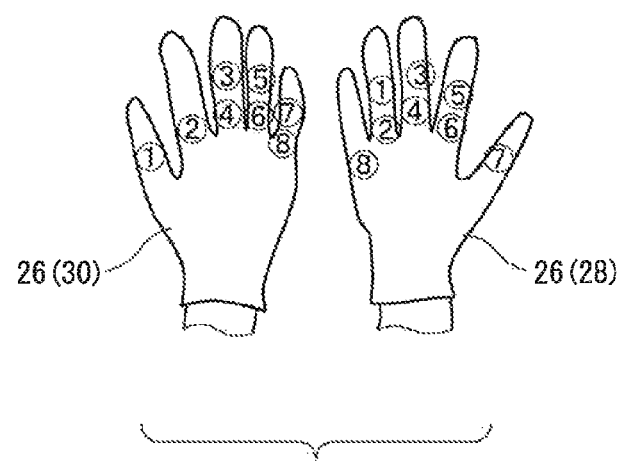
FIG. 5 is a view showing one example of the selected measurement region.

FIG. 5 shows example of determined measurement regions. FIG. 5 shows both hands of a person who wears gloves 26. FIG. 5 is a view showing the palm side. In the example of FIG. 5, eight points of a right hand 28 and eight points of a left hand 30 are selected as measurement regions. Sensors are attached to the measurement regions.

A specific example of the method for selecting a measurement region will be described hereinafter.

With the selection of measurement regions, influence of force to be obtained in practice swinging is limited, and force generated in actual hitting tends to dictate a measurement result. Thus, the correlation with the hit feeling tends to be obtained. On the other hand, if selection of a measurement region is performed excessively, data is apt to depend on local force, which thus deteriorates the correlation with the hit feeling on the contrary. A measurement region is selected in an appropriate range considering the correlation with the hit feeling and the like. In an embodiment to be described hereinafter, an integrated value SF (increased amount Psum and the like) is calculated based on a sum of measured force. This is to understand force on the whole and to improve the correlation with the hit feeling.

Figure 6:
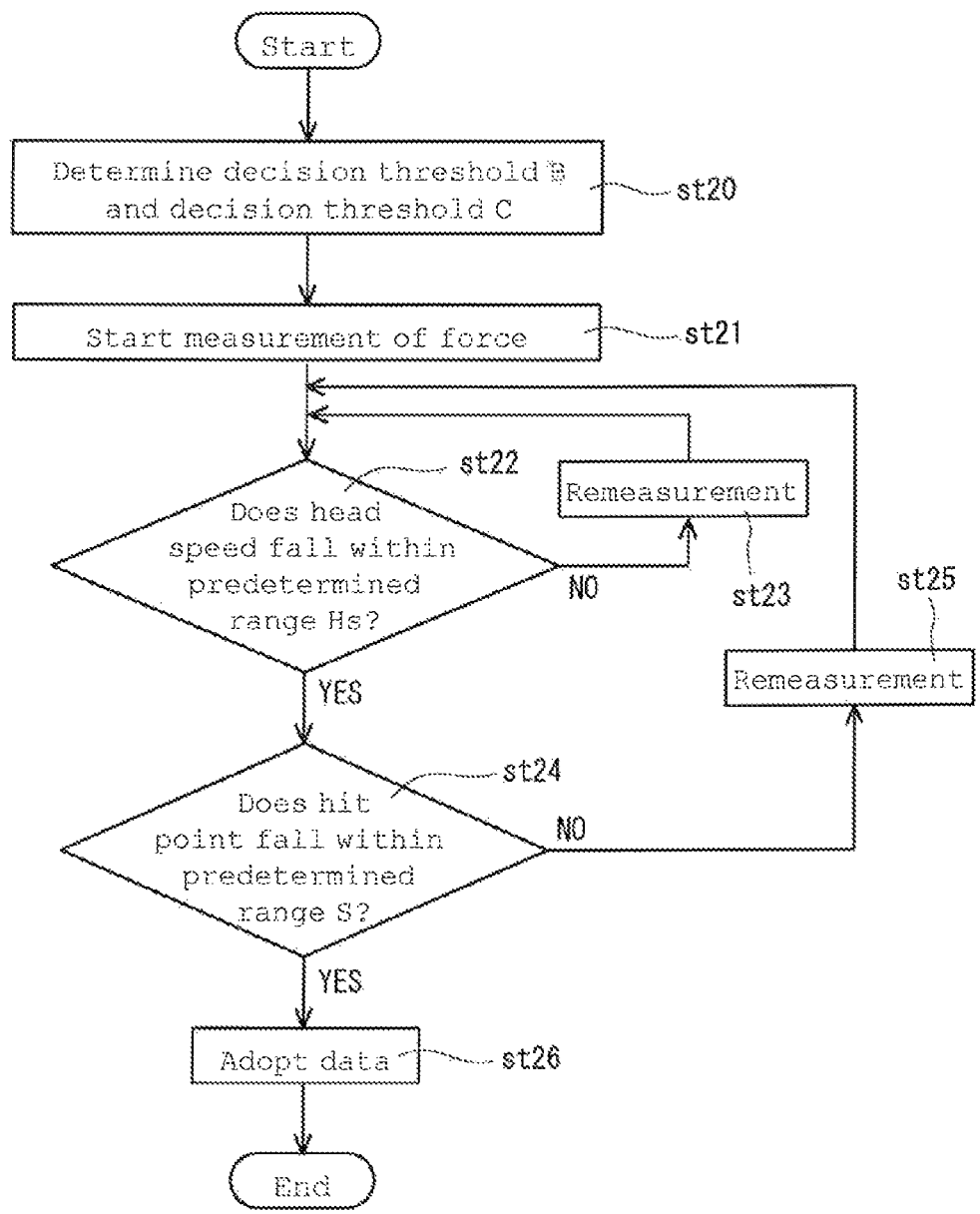
FIG. 6 is a flow chart showing one example of a method for uniformizing measurement conditions, which is a preferred embodiment.

In data measurement according to the present invention, preferably, data is sorted in consideration of ball hitting conditions. FIG. 6 is a flow chart showing one example of a procedure for sorting the data.

In the method for sorting data, a decision threshold B and a decision threshold C are determined first (step st20). The threshold B is a range of variations in head speeds, and for example, a range Hs to be described hereinafter. The threshold C is a range of variations in hit points (hit ball positions), and, for example, a predetermined range S to be described hereinafter. The smaller the threshold B or the threshold C are, the fewer the variations in the hitting conditions are, and data reliability can be thus improved. On the other hand, when a swing subject h1 is a person, in particular, acquisition of data that can be adopted may become difficult if the threshold B and the threshold C are excessively small. These circumstances are considered in determining the threshold B and the threshold C, for example.

Next, measurement of force is performed (step st21). The measurement of force is measurement by actual hitting. Preferably, the measurement of force is one example of the step st200 mentioned above. Then, it is determined whether a head speed falls within a predetermined range Hs (step st22). If the head speed is out of the predetermined range Hs, measurement of force is performed again (step st23). If the head speed falls within the predetermined range Hs, it is further determined whether a hit point falls within a predetermined range S (step st24). If the hit point is out of the predetermined range S, measurement of force is performed again (step st25). If the hit point falls within the predetermined range S, the data is adopted (step st26).

The predetermined range S mentioned above is not specifically limited, it may be, for example, a "range in which a distance from a face center is within D mm", "range in which a distance from a sweet spot is within D mm", "range whose radius is D mm" and the like. When the swing subject h1 is a person, variations in hit points are generated inevitably. Thus, when the swing subject h1 is a person, excessively limiting the predetermined range S may make it difficult to obtain a necessary number of data pieces. From this standpoint, for example, the D above can be set to equal to or greater than 2 mm, furthermore equal to or greater than 5 mm, and furthermore equal to or greater than about 7 mm. Although no limit is set on an upper limit of the D, it can be set to equal to or less than 10 mm, for example, from the standpoint of reliability. When the swing subject h1 is a swing robot, the above D can be further reduced as variations in hit points are fewer. In this case, for example, D) can be set to equal to or less than 5 mm, and furthermore equal to or less than 3 mm.

The head speed mentioned above is one example of a swing speed. It is preferable to limit the swing speed to a predetermined range Hs from the standpoint of uniformizing measurement conditions and obtaining reliable data.

The hit point and the swing speed can correlate with force. Because of the structure of a golf club, a ball fitting face does not exist on an extended line of a shaft axis line. Thus, when a ball is hit, a rotational moment is generated around the shaft axis line, and the golf club tries to rotate around the shaft axis line. In order to prevent a slip of a grip due to the rotational moment, the swing subject may possibly hold the grip strongly (without thinking). The swing speed and the hit point may affect the grip face due to some factor including this factor.

When a swing robot is used as a swing subject, uniformity in the swing speed and, uniformity in the hit point are high. Use of the swing robot may eliminate the need for sorting of measurement data as described above.

Figure 7:
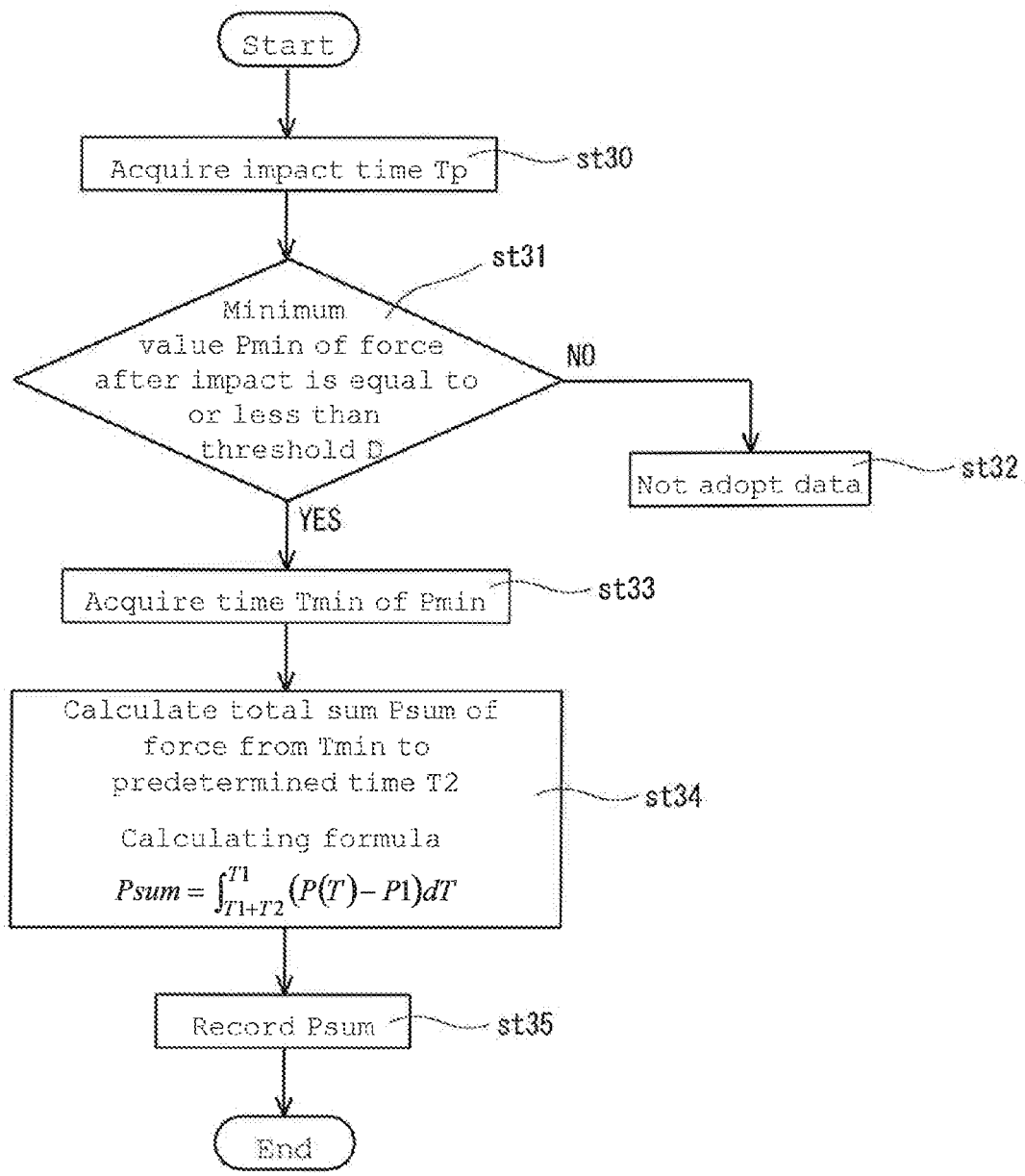
FIG. 7 is a flow chart showing one example of a data analysis method, which is a preferred embodiment.

FIG. 7 shows a flow chart showing a preferred example of data analysis (step st300) mentioned above. In the data analysis, impact time Tp is first obtained step st30). A method for obtaining the impact time Tp is not limited. As described hereinafter, the impact time Tp can be distinguished based on measured chronological force data. In addition, as the impact time Tp is time when a ball hits, it can also be recognized by an image, hitting sound, and the like. The impact time Tp can be obtained with various methods including these methods.

Next, it is determined whether a minimum value Pmin of the force at time later than the impact time Tp is equal to or less than a threshold D (step st31). As shown by data to be described hereinafter, force may temporarily drops immediately after the impact time Tp. The temporary drop of force may be used as information for determining whether the data is normal. If the minimum value Pmin of the force at time later than the impact time Tp exceeds the predetermined threshold D, the data may be rejected (step st32).

If the minimum value Pmin of the force at time later than the impact time Tp is equal, to or less than the predetermined threshold D, the data is adopted. Then, time when the force is the minimum value Pmin can be obtained (step st33).

If time when the force reaches the maximum between the impact time Tp and, time after 50 msec elapses is Tmax, preferably, the time Tmin is defined as time when the force reaches the minimum between the impact time Tp and the time Tmax. It was learned that a correlation of an increased amount Psum to be described hereinafter and the hit feeling is relatively high if the time Tmin is set in this manner. An evaluation based on the increased amount Psum is one example of an evaluation based on the integrated value Sf.

Next, in chronological data of measured force, an increased amount Psum from the time Tmin to the time T2 is calculated (step st34). The total sum Psum is calculated based on a time-related integrated value of a function having time and force as variables. The integrated value is an integrated value in a specific interval Z12 from the time T1 after the impact to the time T2. The time Tmin is a preferred example of the time T1. The analysis based on the increased amount Psum is a preferred example of analysis based on the integrated value Sf.

The time T2 is not limited as far as it is later than the time T1. A preferable example of time T2 is time Tmax when the force reaches the maximum at time later than the impact time Tp.

Although a period from the time T1 to the time T2 (specific interval Z12) is not limited, it may be preferably equal to or more than 5 msec, and more preferably, equal to or more than 10 msec, from the standpoint of a correlation with the hit feeling. On the other hand, as grip force during a follow-through is apt to vary, the correlation with the hit feeling tends to decrease if the period is too long. From this standpoint, the time from the time T1 to the time T2 (specific interval Z12) is preferably equal ma or less than 100 msec, more preferably equal to or less than 50 msec, and further more preferably equal to or less than 25 msec.

Preferably, a total sum Psum (increased amount) obtained can be recorded (step st35) shown by data to be described hereinafter, it was learned that the total sum Psum can correlate with the hit feeling.

The preferred invention is a method for quantitatively evaluating hit feeling of a sport hitting tool, including a first step, by using measurement means M1 which can measure force Fs acting between a swing subject and the sport hitting tool, obtaining value of the force is at time after the impact, and a second step of determining hit feeling on the basis of the values of the force Fs at least at one of the times. The value of the force is at least at one of the times can correlate with the hit feeling. Note that time after the impact includes the impact time Tp.

Other preferred invention is a method for quantitatively evaluating hit feeling of a sport hitting tool, including a first step, by using measurement means M1 which can measure force Fr acting between a swing robot and the sport hitting tool, obtaining value of the force Fs at time after the impact, and a second step of determining hit feeling on the basis of the value of the force Fr at least at one of the times. The value of the force Fr at least at one of the times can correlate with the hit feeling.

Preferably, in the first step, not only values of the force Fs or the force Fr at a specific interval Z12 from time T1 to time T2 after the impact are obtained chronologically, but also hit feeling is determined on the basis of an integrated value Sf of the force Fs or the force Fr in the specific interval Z12.

It was learned that, other than the integrated value Sf, a change rate Rd can be listed as an index having an excellent correlation with the hitting feeling. The change rate Rd is a change rate in the force Fs or the force Fr in the specific interval Z12.

Preferably, the time T1 is defined as time Tmin when the force Fs or the force Fr reaches the minimum. In this case, the correlation with the hit feeling can be improved. It was learned that a phenomenon that the force Fs or the force Fr drops immediately after the impact occurs. Then, the time Tmin being considered the T1 may contribute to improvement of the correlation with the hit feeling.

From the standpoint of the correlation with the hit feeling, the time Tmin may be in a period between the impact time Tp and the impact time Tmax.

As shown in the above embodiment, preferably, the measurement means M1 includes a force sensor provided in at least one of a swing subject or the sport hitting tool. Preferably, a position where the force sensor is installed is determined on the basis of a comparison of a distribution Dp of the force Fs or the force Fr in practice swinging and a distribution Ds of the force Fs or the force Fr in actual hitting. It is believed that data to be observed in practice swinging has a low correlation with the hit feeling. Thus, with the comparison of the distribution Dp and the distribution Ds, a part which has a hither correlation with the her feeling can be selected. Installation of the sensor at a position where a difference between practice hitting and actual hitting enables acquisition of data which is highly correlated with the hit feeling.

As described above, a moment around the shaft axis line is generated when a ball is hit. A golf club tries to rotate around the shaft axis line due to the moment. A slip may occur between a swing subject and a sport hitting tool due to the rotation. A human body may possibly sense size of the slip and adjust the grip force without thinking. It is likely that as the human body feels that the slip is larger, it may increase holding force. It is presumed that the unconscious adjustment of the grip force creates a correlation with the hit feeling.

When the swing subject is a swing robot, there is no unconscious adjustment of the grip force. However, even in the case of the swing robot, the grip force may vary due to the impact. One example of a factor of the variation is the moment around the shaft axis described above. In addition, the shaft may have torsional vibration or flexural vibration due to the impact. The grip force may also vary due to the vibration. It is also presumed that the variation in the grip force creates a correlation with the hit feeling and the grip force.

The measurement means M1 may include a pressure sensor, a three-axis force sensor, and a six-axis force sensor. A preferred pressure sensor is shaped like a sheet. A three-axis force sensor can measure both pressure (force in a z axis in FIG. 3) and shear force (force along an xy plane in FIG. 3). The six-axis force sensor can measure torque in aeon axis, in addition to force in three axial directions.

A commercially available sensor may be used as the measurement means M1. Commercially available three-axis force sensors include, for example, "Dyn Pick" (product name) (for three-axis measurement) of WACOH-TECH Inc. Commercially available six-axis force sensors include "Dyn. Pick" (product name) (for six-axis measurement) of WACHO-TECH Inc., for example.

EXAMPLES

In the following, effects of the present invention will be clarified by examples. However, the present invention should not be interpreted in a limited way on the basis of the description of the examples.

[Test 1] Selection of a Measurement Region (Steps Mentioned Above from st10 to st14)

Pressure sensors are attached to an entire surface of a grip portion of a golf club. As the sensors, "Pinch-A3-4" (product name) manufactured by Nitta Corporation was used. A sensor part of the sensor does not have an area which covers the entire surface of the grip, but has an area which covers a half Peripheral surface of the grip. Thus, measurement for which the sensor part was provided in an upper half of the peripheral face of the grip and measurement for which the sensor part was provided in a lower half of the peripheral face were made. Through these two measurements, measurement of pressure on the entire surface of the contact portion was done.

Figure 8:
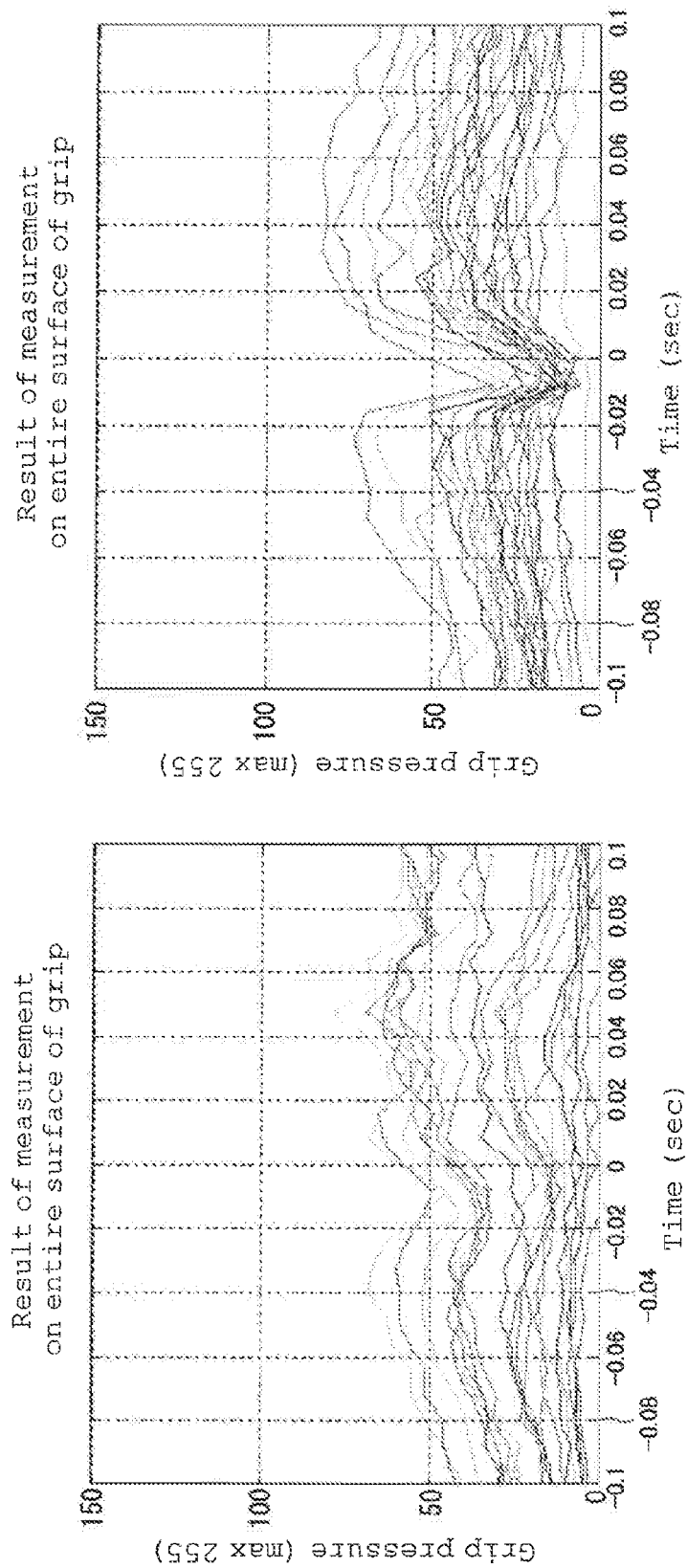
FIG. 8 shows a measurement result for selecting a measurement region, which is data on the vicinity of the second joint of the middle finger of the right hand.
Figure 9:
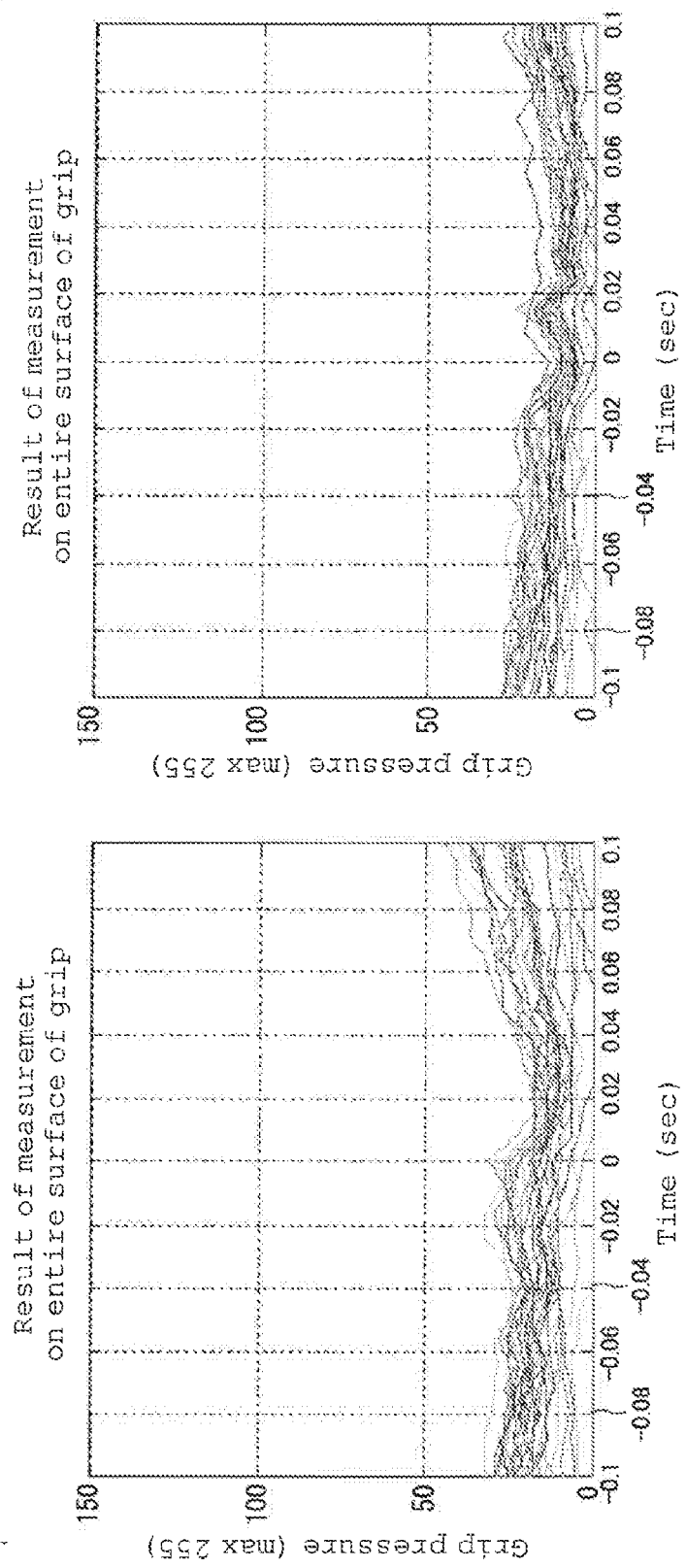
FIG. 9 shows a measurement result for selecting a measurement region, which is data on the vicinity of the first joint of the little finger of the left hand.

FIG. 8 and FIG. 9 show a part of measurement results on the entire surface of the contact portion. In these figures, the left graph shows measurement results of practice swinging and the right graph shows measurement results of actual hitting. When a difference between the left graph and the right graph is large, the region is selected. In addition, each of graph lines in FIG. 8 and FIG. 9 shows each of measured values at a number of pressure measurement elements provided on the sensor manufactured by Nitta Corporation. The horizontal axis of the graph represents time, and the vertical axis of the graph represents pressure.

FIG. 8 is a part of measurement results of a tester K. FIG. 8 shows data on the vicinity of the second joint of the middle finger of the right hand.

As shown in the graph of FIG. 8, a difference between practice swinging and actual hitting is observed, in data of the tester K. Also for other regions, it was determined that there was a difference between practice swinging and actual hitting. Besides the graph in FIG. 8, graphs for respective regions were obtained. Based on these graphs, a region in which a difference between practice swinging and actual hitting was particularly large was determined. With the measurements, a region in which a difference between practice swinging and actual hitting is particularly large can be selected. In the selection, the above threshold A is not specifically limited, and can be determined as appropriate so that a correlation of the Psum or the change rate Rd and the hit feeling will be high.

FIG. 9 is a part of measurement results of a tester S FIG. 9 is data on the vicinity of the first joint of the little finger of the left hand.

As shown in the graph of FIG. 9, a difference between practice swinging and actual hitting is observed, also in data of the tester S. Also for other regions, it was determined that there was a difference between practice swinging and actual hitting. Besides the graph in FIG. 9, graph for each of the regions was obtained. Based on these graphs, a region in which a difference between practice swinging and actual hitting was particularly large was determined. With the measurements, a region in which a difference between practice swinging and actual hitting is particularly large can be selected. In the selection, the above threshold A is not specifically limited, and can be determined as appropriate so that a correlation of the Psum or the change rate Rd or [Fmax−Fmin] and the hit feeling will be high.

Although the pressure sensor was used here, other sensor may be used. For example, a sensor capable of measurement of shear force may be used. Sensors capable of measurement of shear force include the three-axis force sensor or the six-axis force sensor described above. For example, a plurality (multiplicity) of three-axis force sensors are arranged, and selection of a measurement region can be performed based on data of the plurality of three axis force sensor. From the standpoint that it enables a wide range of measurement, use of the pressure sensor is preferred in the selection of a measurement region.

[Test 2] Measurement 1 of Grip Force through Actual Hitting

In the test 2, the measurement of grip force in actual hitting (step st200 mentioned above) and the data analysis (step st300 mentioned above) were made. Pressure was adopted as grip force. As a pressure measuring system including a pressure sensor shaped like a pressure sheet, "Octosense" (product name) (Item No. 08107B00) manufactured by Nitta Corporation was used. The "Octosense" is a wired pressure measuring system. Each "Octosense" has eight sensor parts. Two "Octosense" were used. A first "Octosense" was used for a right hand, and eight sensor parts were disposed on the right hand. A second "Octosense" was used for a left hand, and eight sensor parts were disposed on the left hand. The sensor parts were disposed on the sixteen points shown in FIG. 5. These sensor parts were attached on golf gloves. The sixteen points are regions in which the difference between the practice swinging and the actual hitting is relatively large in the measurement of the test 1. The measured pressure is the force Fz.

Two high speed cameras synchronized with each other were used to detect impact time Tp and to enable determination of a time axis of measurement data of the "Octosense". Since the "Octosense" had no synchronization feature, one of the two high speed cameras was caused to photograph a LED lamp which emits light simultaneously with start of measurement of the "Octosense", while the other camera was caused to photograph a moment of collision impact) of a ball with a head.

A tester was a golf player A. A sampling frequency of pressure measurement was set to 200 Hz. A wedge was used as a golf club. Simultaneously with the pressure measurement, a head speed was measured, and only data when the head speed was 16.0 m/s or more and 18.0 m/s or less was adopted. Specifically, the predetermined range Hs was set to 16.0 m/s or more and 18.0 m/s or less. The head speed range corresponds with the head speed of the wedge in an approach shot. It has been known that in such an approach shot the hit feeling can be easily obtained.

Simultaneously with the pressure measurement, a high speed camera photographed swings. The impact time Tp was detected based on an image obtained by the photographing of swings.

Four hits by the golf player A were measured.

Figure 10:
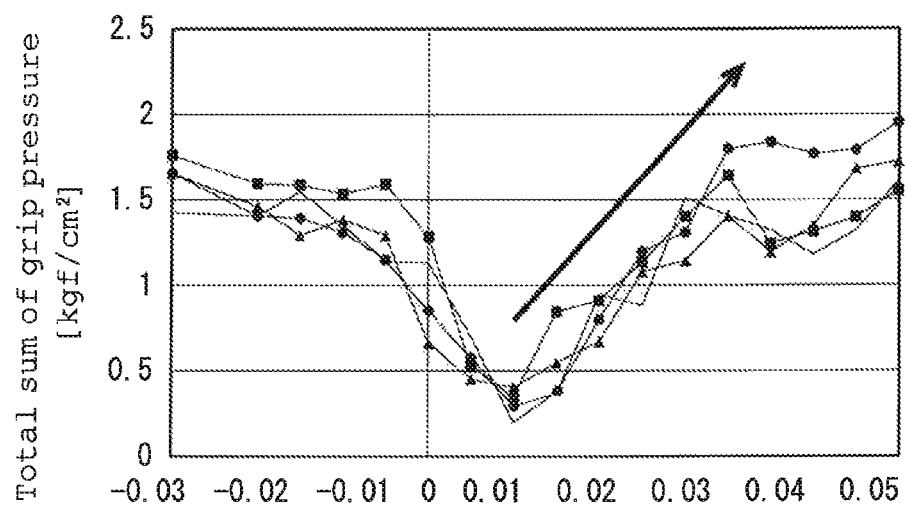
FIG. 10 is a graph showing one example of chronological measurement data of grip pressure.
Figure 11:
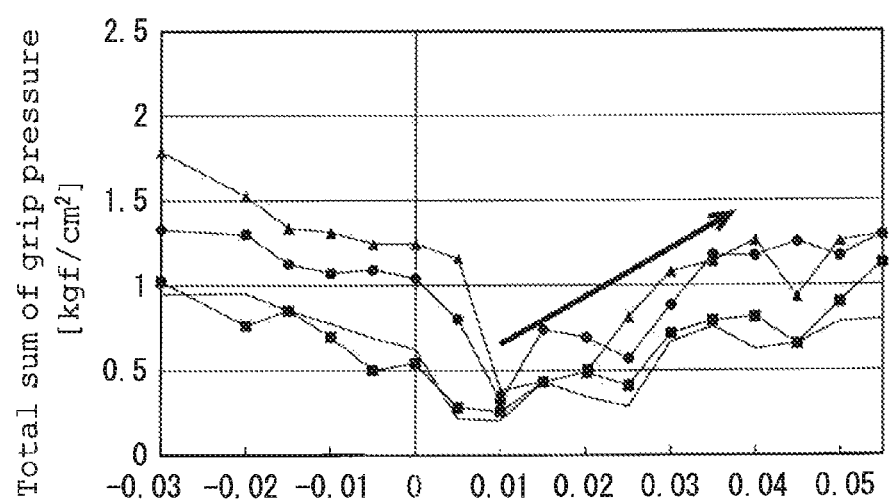
FIG. 11 is a graph showing other one example of chronological measurement data of grip pressure.

FIG. 10 shows measurement results of balls sensuously evaluated as having and hitting ball feeling. A horizontal axis is time and a vertical axis is pressure (a total sum of pressures of sixteen points). Data for the four times is shown by four graphs. FIG. 11 shows measurement results of balls sensuously evaluated as having soft hitting ball feeling. A horizontal axis is time and a vertical axis is pressure (a total sum of pressures of sixteen points). Data for the four times is shown by four graphs. A unit of the horizontal axis is "second".

In FIG. 10 and FIG. 11, time zero is the impact time Tp.

As shown in FIG. 10 and FIG. 11, the drop of the grip pressure is observed immediately y after the impact time Tp (about 0.01 second after the impact time Tp). Then, the change rate from the pressure drop time of FIG. 10 is larger than that of FIG. 11. Specifically, the change rate Rd of FIG. 10 is larger than that of FIG. 11. Thus, the hit feeling and the change rate Rd are correlated. It is believed that the harder the hit feeling is, the larger the change rate Rd is, while the softer the hit feeling is, the smaller the change rate Rd is.

[Test 3] Pressure Measurement 2 in Actual Hitting

Measurement was performed using the same pressure sensor as that of the test 2. A tester was a golf player B. A sampling frequency for pressure measurement was set to 1000 Hz. A wedge was used as a golf club and data when the head speed was 16.0 m/s or more and 18.0 m/s or less was adopted. The higher the sampling frequency is, the more number of measurement data pieces per unit time is obtained, and data precision can be thus improved. From this standpoint, the sampling frequency for pressure measurement is preferably equal to or greater than 100 Hz, more preferably equal to or greater than 200 Hz, and still more preferably equal to or greater than 1000 Hz.

Simultaneously with the pressure measurement, a high speed camera photographed swings. The impact time Tp was detected by the photographing of swings. The impact time Tp was defined as time zero.

Figure 12:
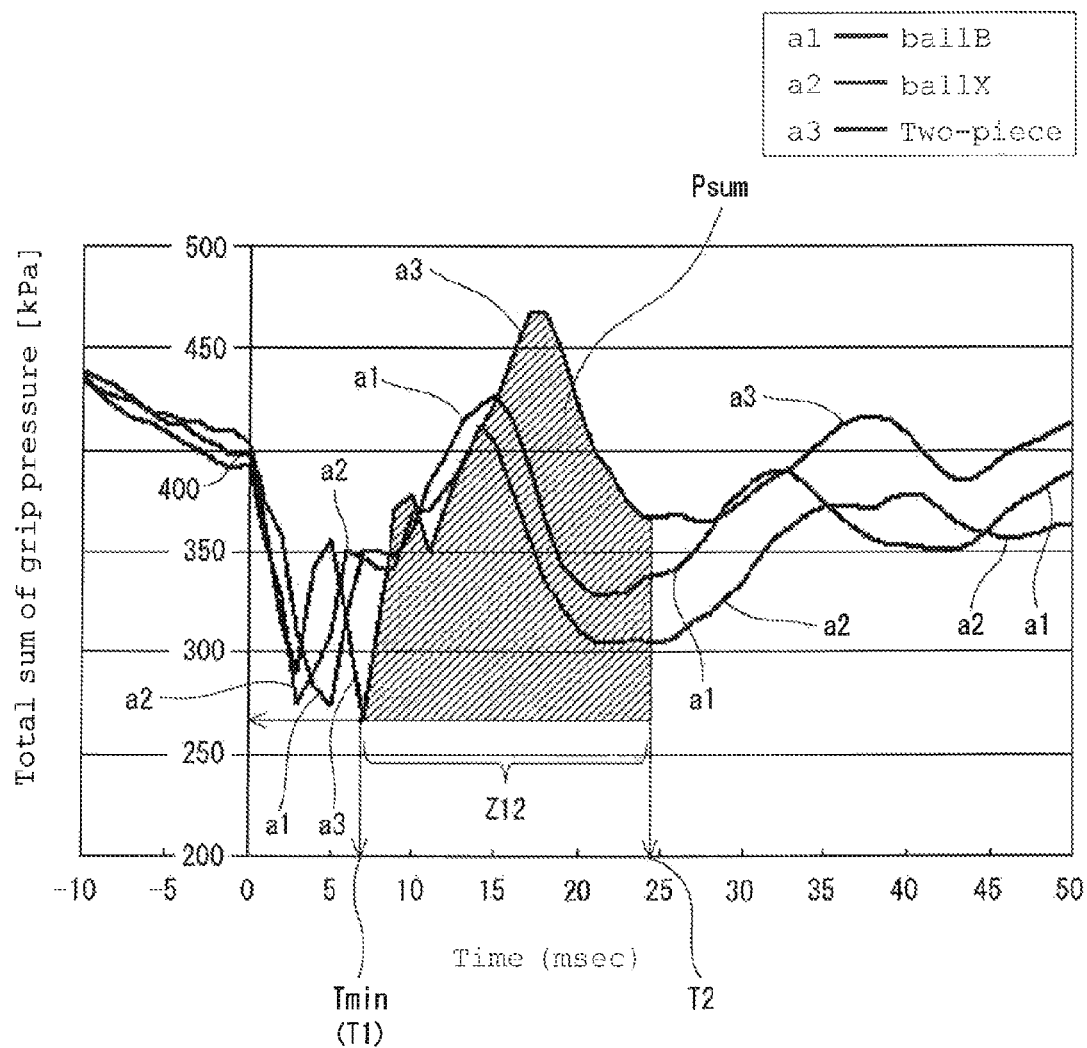
FIG. 12 is a graph showing other one example of chronological measurement data of grip pressure.

FIG. 12 is a graph in which test results of three kinds of balls are overlapped and shown. A horizontal axis line is time and a vertical axis line is a pressure. The pressure is a total sum of data of all sensor parts.

FIG. 12 shows by a symbol a1 measured result of a ball B which is a commercially available item. FIG. 12 shows by a symbol a2 a measured result of a ball X manufactured by SRI Sports Limited. FIG. 12 shows by a symbol a3 a measured result of a two-piece ball which is a commercially available item. Among these three kinds of balls, the two-piece ball is sensuously evaluated as having "hard" hitting ball feeling. On the other hand, the ball B and the ball X are sensuously evaluated as having "soft" hitting ball feeling.

In FIG. 12, as for the data of two-piece ball, Psum in a specific interval Z12 (from time T1 to time T2) is represented as an area of the hatched part. As the time T1, the time Tmin is adopted. It was learned that the Psum is correlated with the hitting ball feeling. It was learned that the correlation that "the greater the Psum is, the harder the hitting ball feeling is" can be obtained.

Figure 13:
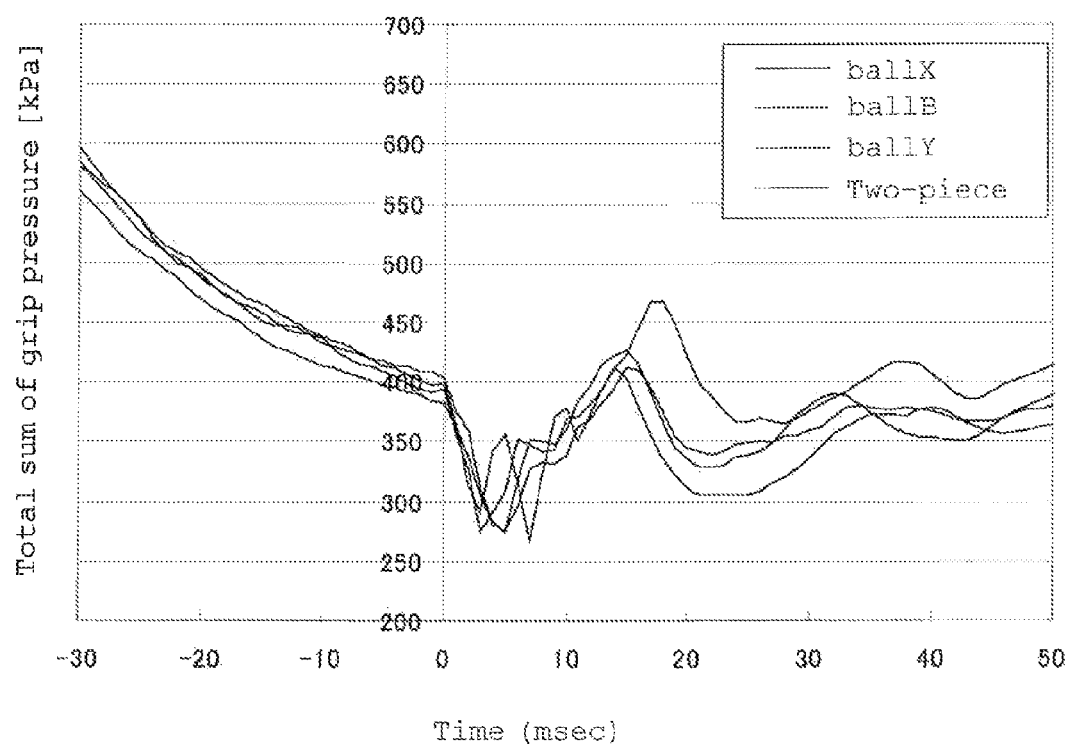
FIG. 13 is a graph showing other one example of chronological measurement data of grip pressure.
Figure 14:
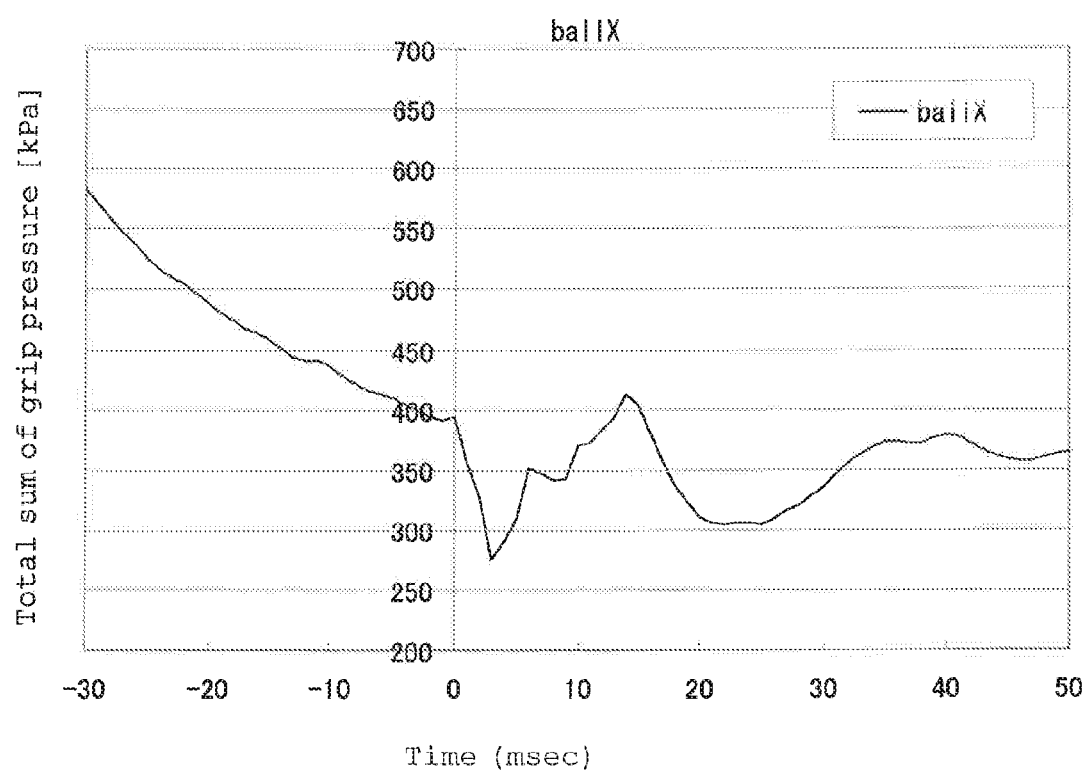
FIG. 14 is a graph showing one of four graph lines shown in FIG. 13.
Figure 15:
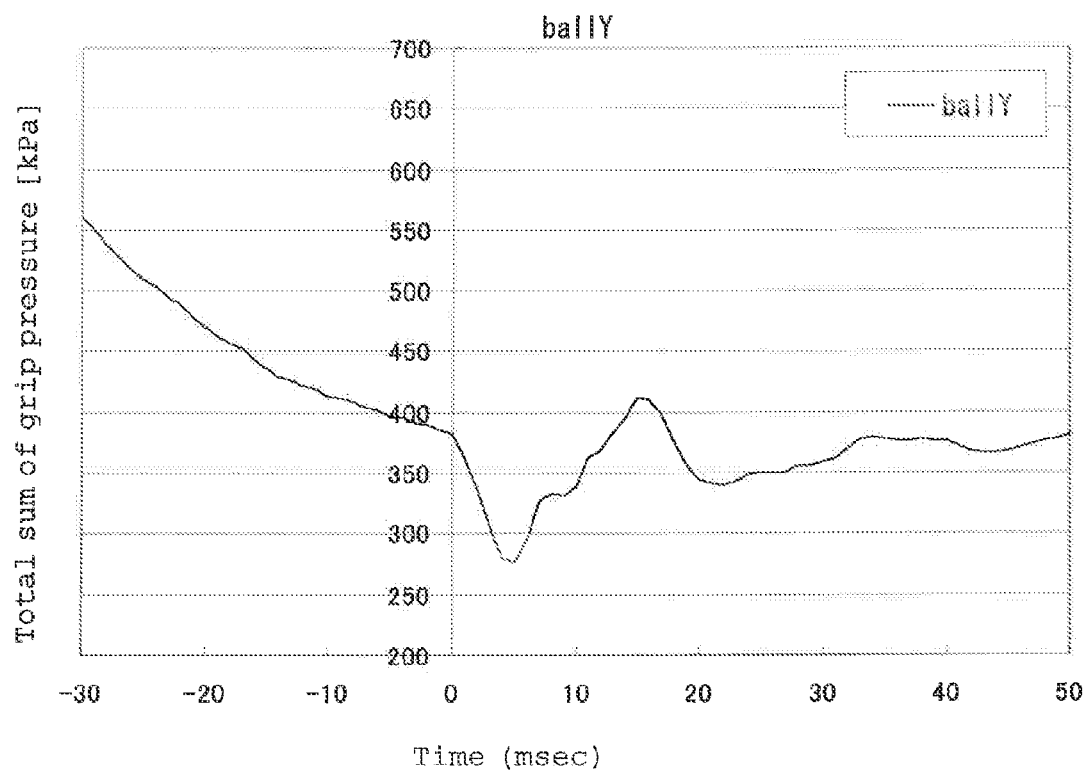
FIG. 15 is a graph snowing other one of the four graph lines shown in FIG. 13.
Figure 16:
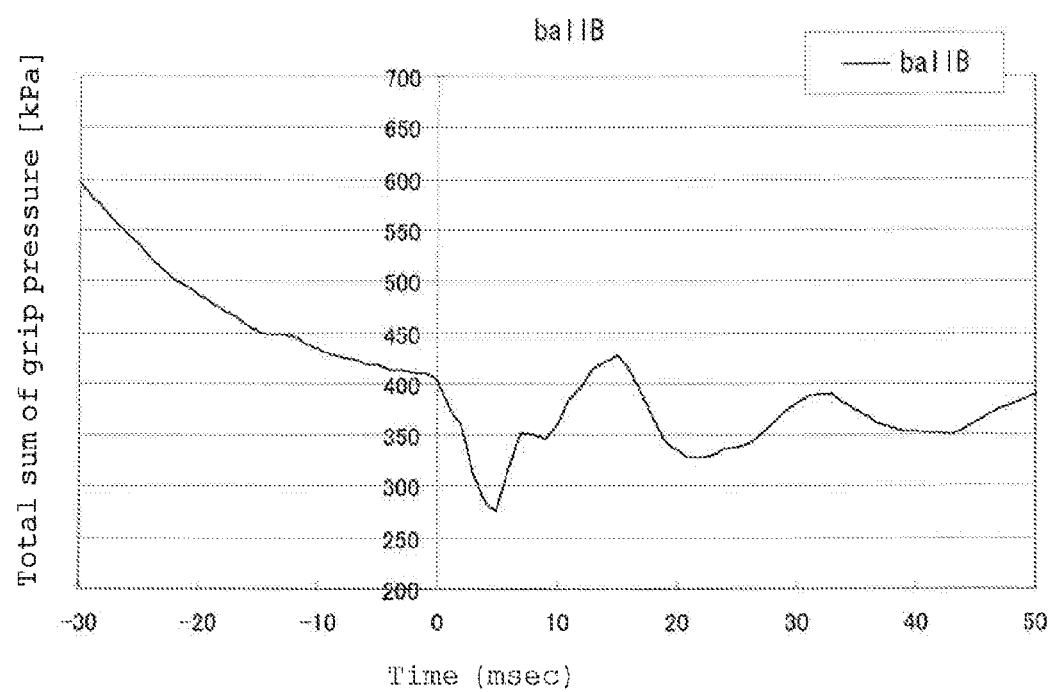
FIG. 16 is a graph showing further other one of the four graph lines shown in FIG. 13.
Figure 17:
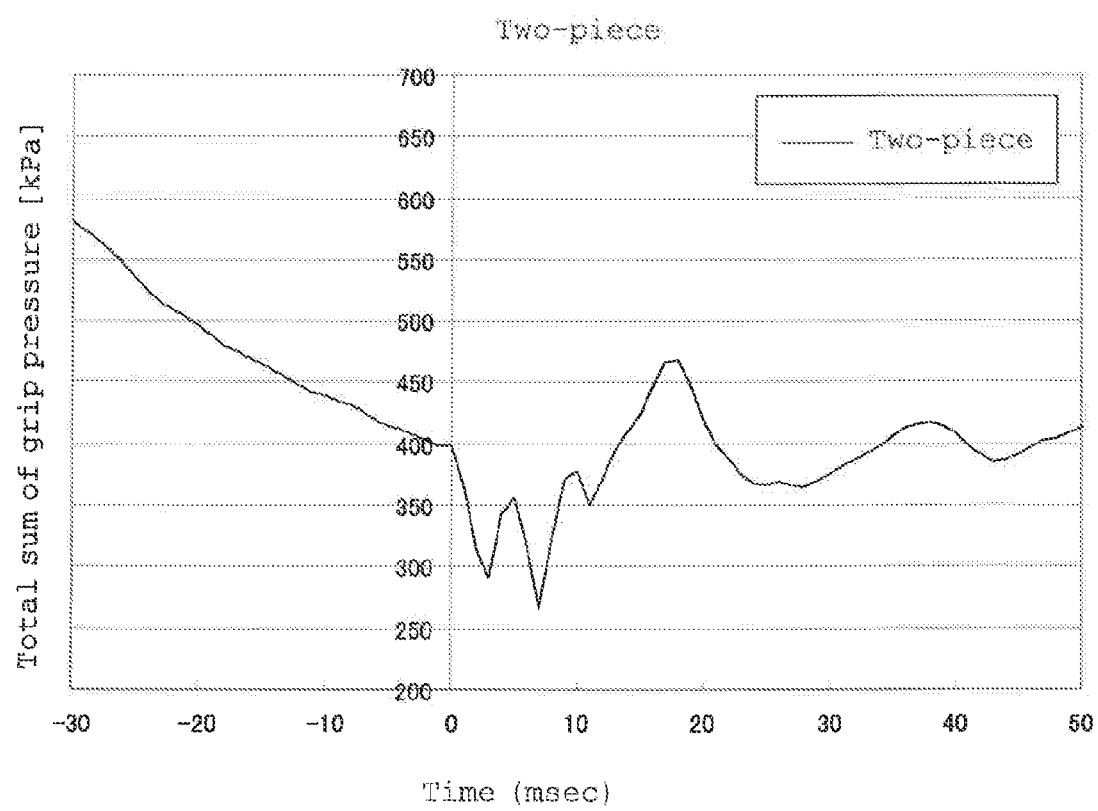
FIG. 17 is a graph showing yet further other one of the four graph lines shown in FIG. 13.

FIG. 13 is a graph based on the same data as that of FIG. 12. In FIG. 13, a test result of one kind of ball is added to the results of the three kinds of balls shown in FIG. 12. Thus, FIG. 13 shows the test results of the four kinds of balls which are overlapped. FIGS. 14 to 17 are graphs, showing the results of each of the four kinds. A horizontal axis line is time and a vertical axis line is a pressure. A unit of the time of the horizontal axis line is msec. The pressure is a total sum of data of all sensor parts.

The balls are the ball B, the ball X, the two-piece ball and, a ball Y manufactured by SRI Sports Limited. As shown in the graph of FIG. 13, the integrated value Sf (Psum) and the change rate Rd of the two-piece ball evaluated as having hard hitting ball feeling tended to be larger than those of the other three kinds of golf balls.

[Test 4] Evaluation Based on Three-Axis Force

Figure 18:
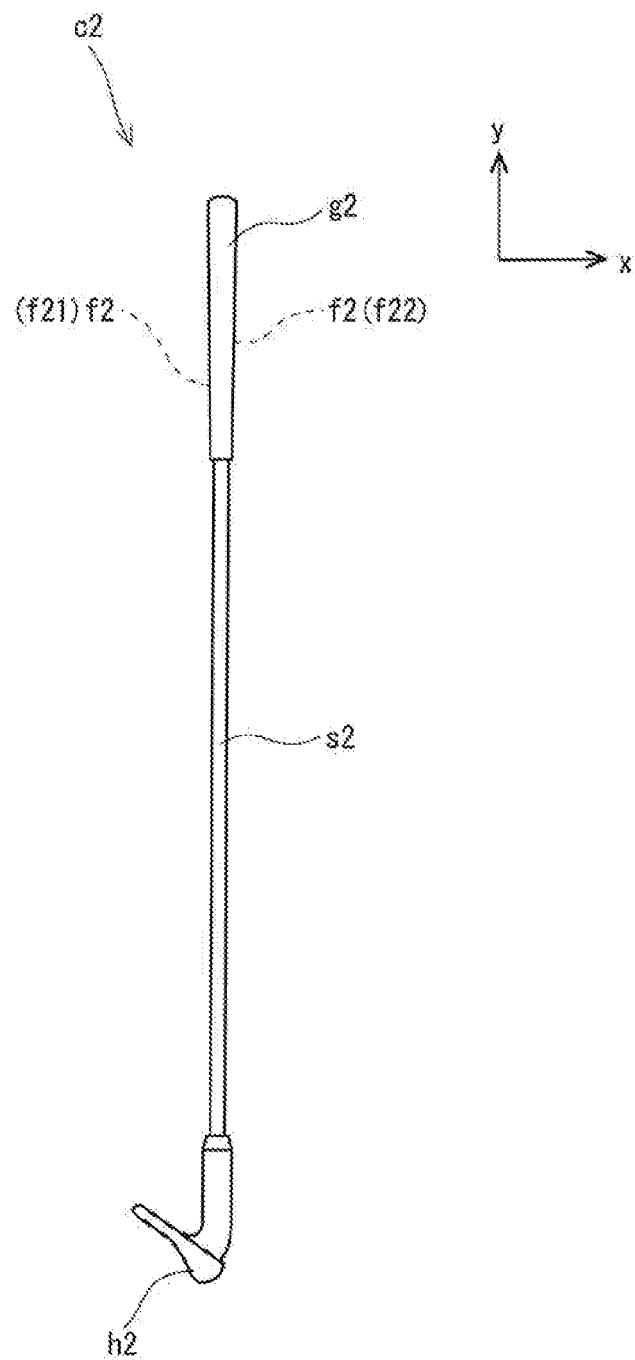
FIG. 18 is a view showing a golf club which has a built-in force sensor to be used in a test.

High-level golf players I and K performed evaluation of the hit feeling based on three-axis force. The golf player is a zero-handicapper and the golf player K also a zero-handicapper. A golf club c2 used in this test was a sand wedge. FIG. 18 shows the golf club c2. In the test 4, the sand wedge manufactured by SRI Sports Limited (product name "SRIXON ZR-800", NS PRO 950 GH Steel Shaft, hardness S) was used.

In addition, the three-axis force means actual force F acting between a swing subject and a sport hitting tool. Thus, the three-axis force has a component in a shear direction. The three-axis force is one example of the force Fs. The three-axis force is one example of the measured value Vf.

The golf club c2 has a head h2, a shaft s2, and a grip g2.

Force sensors f2 were placed inside the shaft of the golf club c2. The force sensors f2 were provided in more than one point. The force sensors f2 were provided in two points. A first force sensor f21 was provided at a position where the third joint of the index finger of the right hand abuts. A second force sensor f22 was provided at a position were the third joint of the index finger of the left hand abuts. These positions were determined based on the method for selecting a measurement region using a pressure sensor (mentioned above).

A throughhole, not shown, which penetrates through the shaft s2 and the grip g2 was provided. A force sensing section of the force sensor f2 was exposed to the external through the use of the throughhole.

A strain gauge, not shown, was used in the force sensor f2. Force was detected as a change in electric resistance of the strain gauge. A plurality of strain gauges was disposed so that force acting in an x axis direction, a y axis direction, and a z axis direction can be measured. The plurality of strain gauges was disposed three-dimensionally. A bridge circuit was incorporated for each axis, and force in each direction was measured by measuring a differential voltage.

As a ball, the ball B, the ball X, and the ball Y were used A sampling frequency for pressure measurement was set to 10 kHz.

A shot marker was attached to a face of the head h2. Hit points were measured with the shot marker. A hit point is a position where a ball hits the face. The hit point was measured for each hit. Simultaneously, three-axis force was measured. Simultaneously, the hitting ball feeling was evaluated for each hit.

Two-dimensional orthogonal coordinates (X axis and Y axis) were set on the face surface. A hit point was represented by the coordinates (X axis and Y axis). The X axis was a toe-heel direction (right-left direction). The X axis was parallel to a face line. The Y axis was an up-down direction. The Y axis was perpendicular to the face line. The Y coordinate at a position which was 16 mm away from the lowest point of the leading edge was defined as 0 mm. The X coordinate at a midpoint of the longest face line was defined as 0 mm.

The hitting ball feeling was evaluated in nine stages from one-point to nine-point. The higher the point means that the hitting ball feeling is harder. The hitting ball feeling is the sensuously evaluation.

From the standpoint of improving test accuracy, data was sorted by a head speed. A head speed was measured for each hit. Measurement data when the head speed was 20.0 m/s or more and 22.0 m/s or less was adopted.

From the standpoint of further improving the test accuracy, data was sorted by a hit point. Measurement data when the X coordinate was −3.0 mm or more and 3.0 mm or less and when the Y coordinate was equal to or more than −4.0 mm was adopted.

After being sorted by the head speed and the hit point, five data pieces for each tester and for each ball were obtained.

The data measured by the force sensor f2 was force Fx in the x axis direction, force Fy in the y axis direction, and force Fs in the z axis direction. The three-axis force was obtained by finding a vector sum of the force in the three directions. Three-axis force variation was calculated on the obtained three-axis force. When a maximum value (scalar amount) of the three-axis force later than the impact is Fmax, and a minimum value (scalar amount) of the three-axis force later than the impact is Fmin, the three-axis force variation as [Fmax−Fmin]. In addition, Fmax was defined as a maximum value of the three-axis force between time T1 and time T2, while Fmin was defined as a minimum value of the three-axis force between the time T1 and the time T2. The time T1 was defined as impact time Tp, and the time T2 was defined as time when 100 msec elapsed after the impact time Tp.

Figure 19:
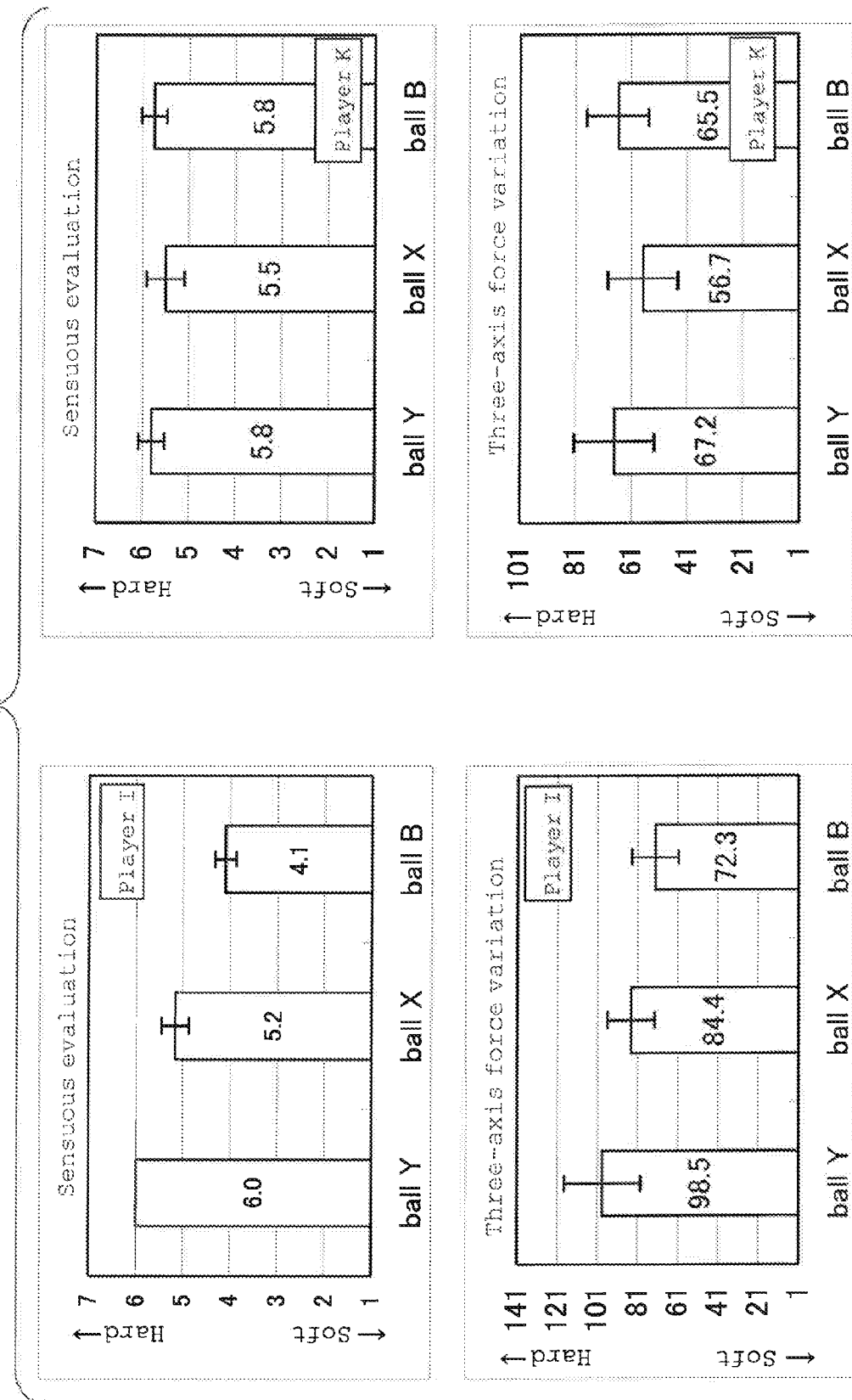
FIG. 19 is a bar graph showing a sensuous evaluation of each ball and three-axis force variation of each ball.

FIG. 19 shows test results of the golf player I and the golf player K. Numeric values shown by the bar graph were average values of the five data pieces. An upper left graph of FIG. 19 shows a result of the hitting ball felling evaluated by the golf player I. A lower left graph of FIG. 19 shows a result of three-axis force variation evaluated by the golf player I. An upper right graph of FIG. 19 shows a result of the hitting ball felling evaluated by the golf K. A lower right graph of FIG. 19 is a result of the three-axis force variation evaluated by the golf player K.

In addition, error bars are added to the bar graphs of FIG. 19. The error bars show a standard deviation.

In the results of the golf player I shown in FIG. 19, the evaluation order in the evaluation on the hitting ball feeling coincides with the evaluation order in the three-axis force variation. The golf player I felt that the ball Y was hardest in the sensuous evaluation and the ball Y had the largest three-axis force variation. The golf player I felt that the ball B was softest in the sensuous evaluation and the ball B had the smallest three-axis force variation.

Also in the results of the golf player K shown in FIG. 19, the evaluation order in the evaluation on the hitting ball feeling coincides with the evaluation order in the three-axis force variation.

The sensuous evaluation order of the golf player K and that of the golf player I differ. Nevertheless, for both golf player I and golf player K, the evaluation order in the evaluation on the hitting ball feeling coincides with the evaluation order in the three-axis force variation. The result shows that there is a good correlation on of the hitting ball feeling and the three-axis force variation.

Figure 20:
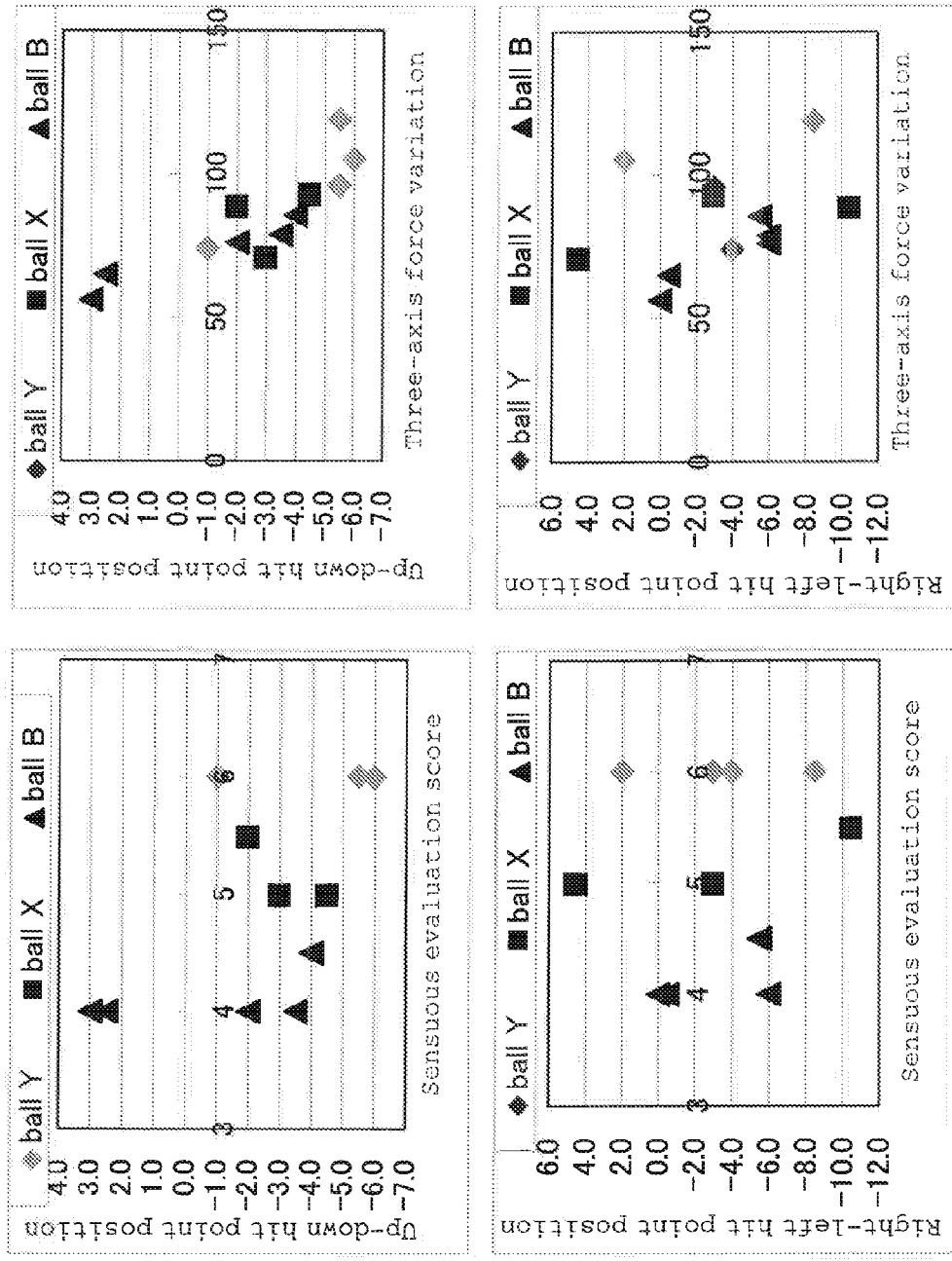
FIG. 20 is a scatter diagram showing a relation of a sensuous evaluation and hit points and a relation of three-axis force variation and hit points.

FIG. 20 shows a result on the hit point of the golf player I.

An upper left graph of FIG. 20 shows a relation of the sensuous evaluation and the hit points in the up-down direction. Specifically, a horizontal axis shows score in the sensuous evaluation, and a vertical axis shows a Y coordinate of the hit point.

A lower left graph of FIG. 20 shows a relation of the sensuous evaluation and the hit points in the right-left direction. Specifically, a horizontal axis shows scores in the sensuous evaluation, and a vertical axis shows an X coordinate of the hit points.

An upper right graph of FIG. 20 shows a relation of the three-axis force variation and hit points in the up-down direction. Specifically, a horizontal axis shows the three-axis force variation, and a vertical axis shows a Y coordinate of the hit points.

A lower right graph of FIG. 20 shows a relation of the three-axis force variation and hit points in the right-left direction. Specifically, a horizontal axis shows the three-axis force variation, and a vertical axis shows an X coordinate of the hit points.

It can be interpreted from the upper left graph of FIG. 20 that there is a negative correlation. Specifically, it can be interpreted that the hit points tend to be higher as the scores of the sensuous evaluation are lower. In other words, it can be interpreted that the hit points tends to be higher as the hitting ball feeling is softer. On the other hand, almost no correlation can be seen from the lower left graph of FIG. 20. According to the results, it is believed that hit point positions in the up-down direction (the Y coordinate mentioned above) have a strong correlation with the hitting ball feeling than hit point positions in the right-left direction (the X coordinate mentioned above).

It can also be interpreted from the upper right graph of FIG. 20 that there is a negative correlation. Specifically, it can be interpreted that the hit points tend to be higher as the three-axis force variation is lower. On the other hand, almost no correlation can be seen from the lower right graph of FIG. 20. According to the results, it is believed that hit point positions in the up-down direction (the Y coordinate mentioned above) have a stronger correlation with the three-axis force variation than hit point positions in the right-left direction (the X coordinate mentioned above).

Figure 21:
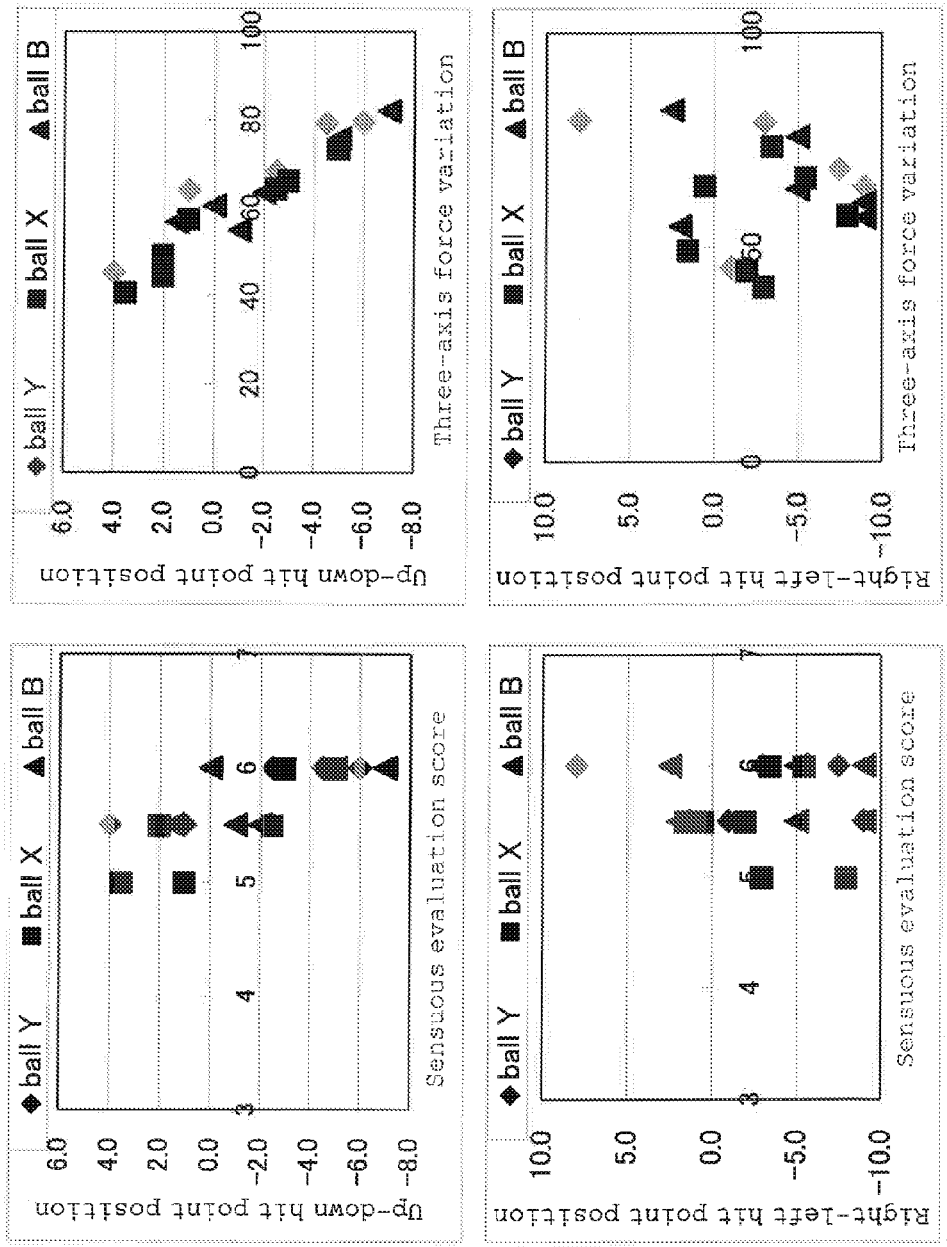
FIG. 21 is a scatter diagram showing a relation of a sensuous evaluation and hit points and a relation of three-axis force variation and hit points.

FIG. 21 shows the result on the hit points of the golf player K. As shown hereinafter, the result of the golfer K shows a similar tendency to that of the golf player I.

An upper left graph of FIG. 21 shows a relation of the sensuous evaluation and the hit points in the up-down direction. Specifically, a horizontal axis shows scores in the sensuous evaluation, and a vertical axis shows a Y coordinate of the hit points.

A lower left graph of FIG. 21 shows a relation of the sensuous evaluation and the hit points in the right-left direction. Specifically, a horizontal axis shows scores in the sensuous evaluation, and a vertical axis shows an X coordinate of the hit points.

An upper right graph of FIG. 21 shows a relation of the three-axis force variation and the hit points in the up-down direction. Specifically, a horizontal axis shows a three-axis force variation, and a vertical axis shows a Y coordinate of the hit points.

A lower right graph of FIG. 21 shows a relation of the three-axis force variation and the hit points in the right-left direction. Specifically, a horizontal axis shows three-axis force variation, and a vertical axis shows an X coordinate of the hit points.

It can be interpreted from the upper left graph of FIG. 21 that there is a negative correlation. Specifically, it can be interpreted that the hit points tend to be higher as the scores of the sensuous evaluation are lower. In other words, it can be interpreted that the hit points tends to be higher as the hitting ball feeling is softer. On the other hand, almost no correlation can be seen from the lower left graph of FIG. 21. According to the results, it is believed that hit point positions in the up-down direction (the Y coordinate mentioned above) have a stronger correlation with the hitting ball feeling than hit point positions in the right-left direction (the X coordinate mentioned above).

It can also be interpreted from the upper right graph of FIG. 21 that there is a negative correlation. Specifically, it can be interpreted that the hit points tend to be higher as the three-axis force variation is lower. On the other hand, almost no correlation can be seen from the lower right graph of FIG. 21. According to the results, it is believed that hit point positions in the up-down direction the Y coordinate mentioned above) have a stronger correlation with the three-axis force variation than hit point positions in the right-left direction (the X coordinate mentioned above).

The results shown in FIG. 20 and FIG. 21 suggest a correlation between the hit points and the hitting ball feeling. In particular, they suggest that the hitting ball feeling is more susceptible to positions in the up-down direction than those in the toe-heel direction. As shown by the results in FIG. 19, the golf Player I and the golf player K had different hitting ball feeling even on the same balls. It is possible that the difference is caused by influence of hit point positions.

As shown by FIG. 19, there was no significant difference in the hitting ball feeling due to a kind of halls. Nevertheless, the evaluation order in the hitting ball feeling coincides with that in the three-axis force variation. A good correlation between the hitting ball feeling and the three-axis force variation was exhibited.

FIGS. 22 to 28 show one example of measurement results of three-axis force. The golf club c2 (sand wedge) mentioned above was used. A tester of the measurement was K. A ball Sf which K felt was soft, and a ball Hd which K felt was hard were used. The ball Sf was the ball X. The ball Hd was the ball Y.

Figure 22:
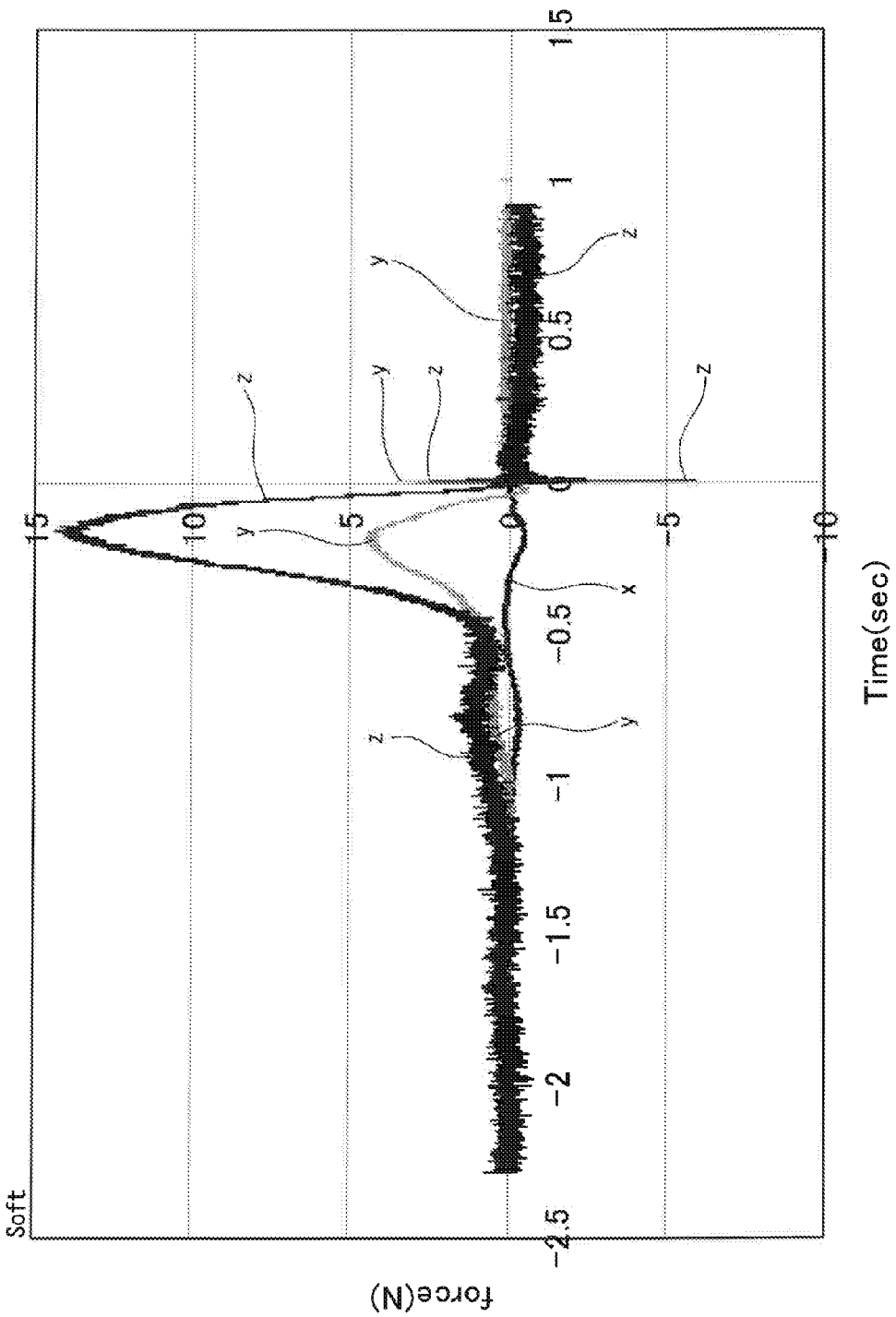
FIG. 22 is a graph showing one example of a measurement result by a force sensor.

FIG. 22 shows a result of measurements using the ball Sf. In FIG. 22, a symbol x represents the Fx, a symbol y represents the Fy, and a symbol z represents the Fz. A horizontal axis is time, and the impact time Tp is defined as 0. A vertical axis is force (N).

Figure 23:
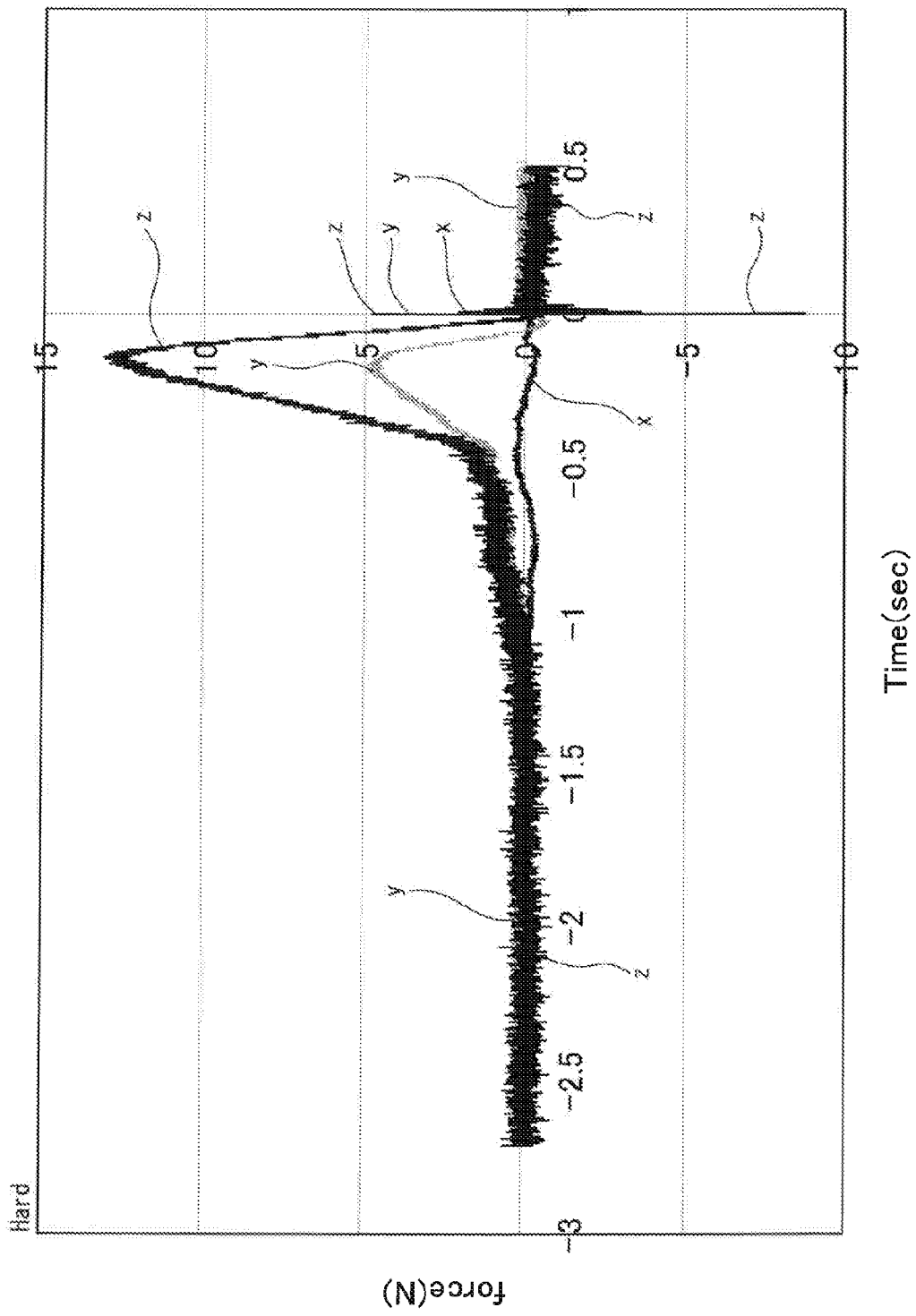
FIG. 23 is a graph showing one example of a measurement result by a force sensor.

FIG. 23 shows a result of measurement using the ball Hd. In FIG. 23, a symbol x represents the Fx, a symbol y represents the Fy, and a symbol z represents the Fz. A horizontal axis is time, and the impact time Tp is defined as 0. A vertical axis is force (N).

Figure 24:
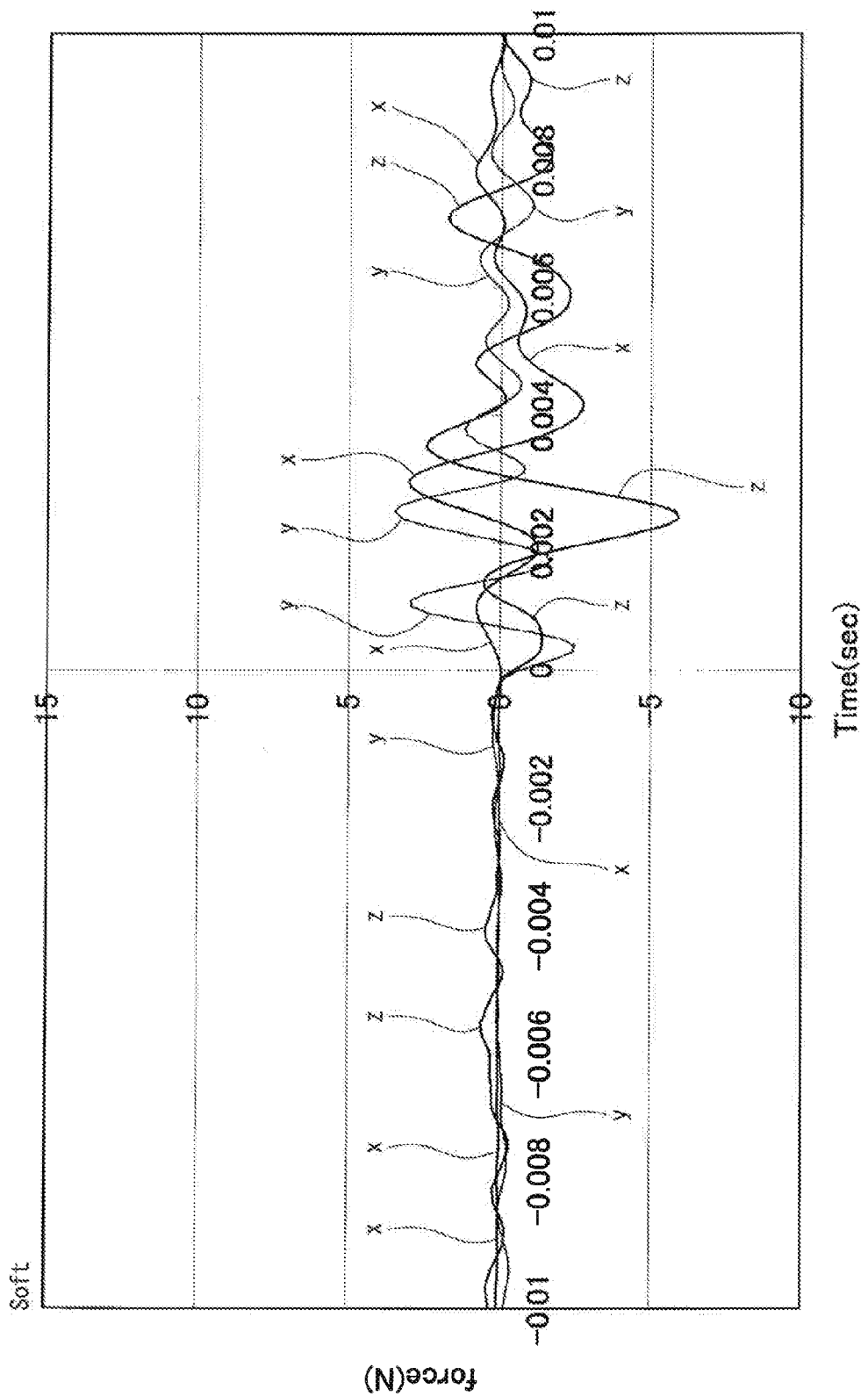
FIG. 24 is an enlarged view of FIG. 22.
Figure 25:
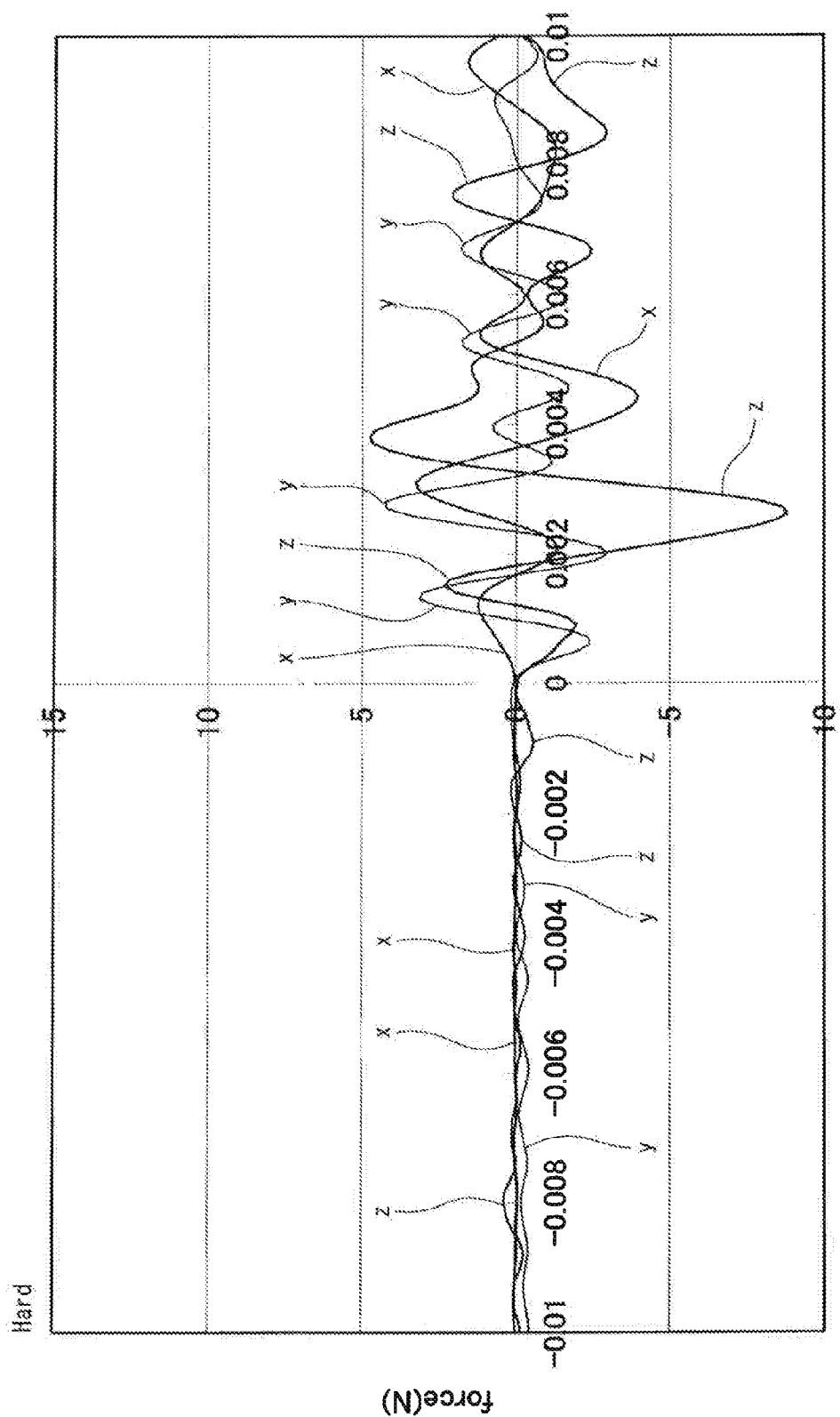
FIG. 25 is an enlarged view of FIG. 23.

FIG. 24 shows a result of measurement using the ball Sf, and is an enlarged view of FIG. 22, FIG. 25 is a result of measurement using the ball Hd, and is an enlarged view of FIG. 23.

Figure 26:
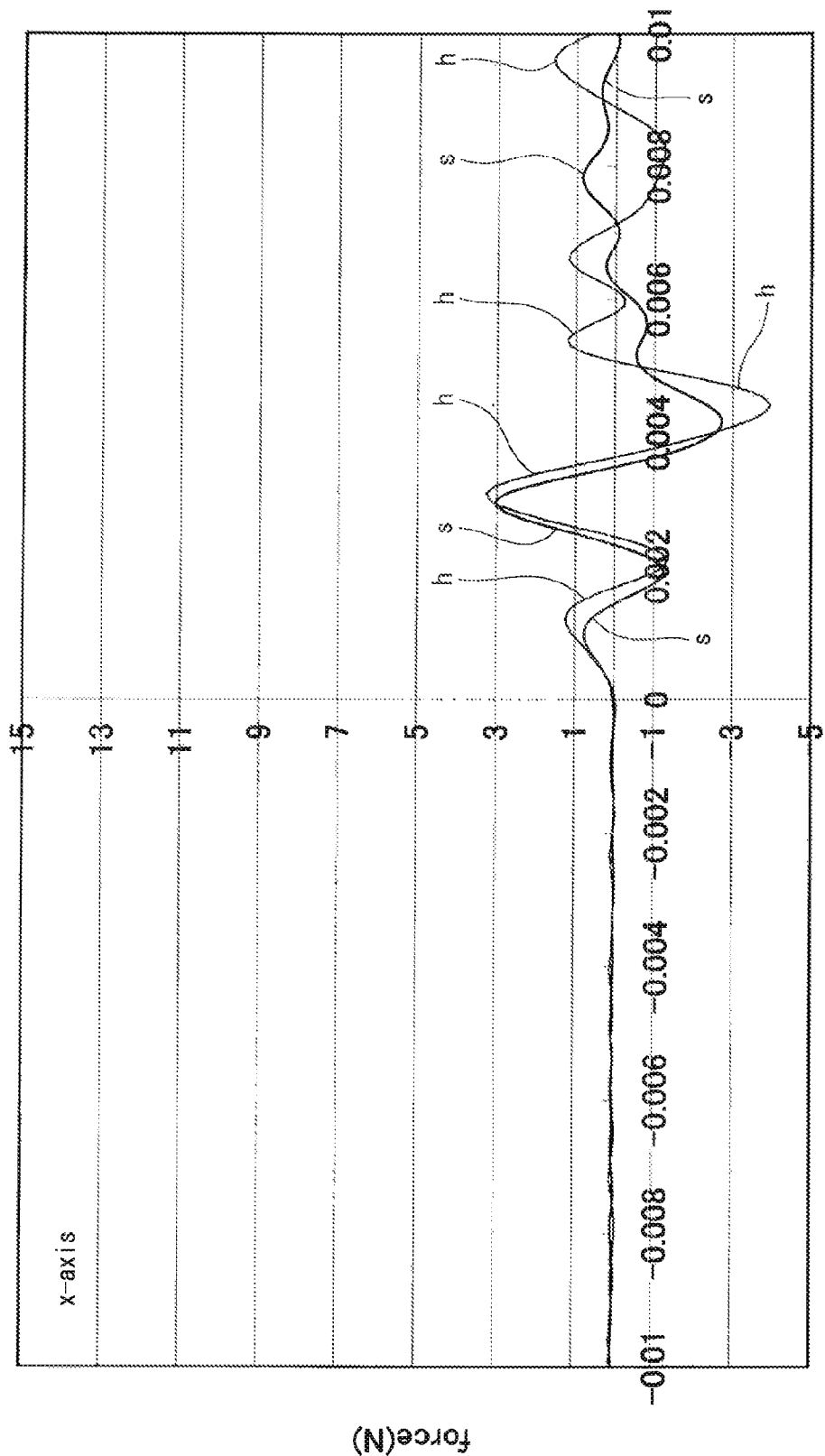
FIG. 26 is a graph showing force in an axis x direction.
Figure 27:
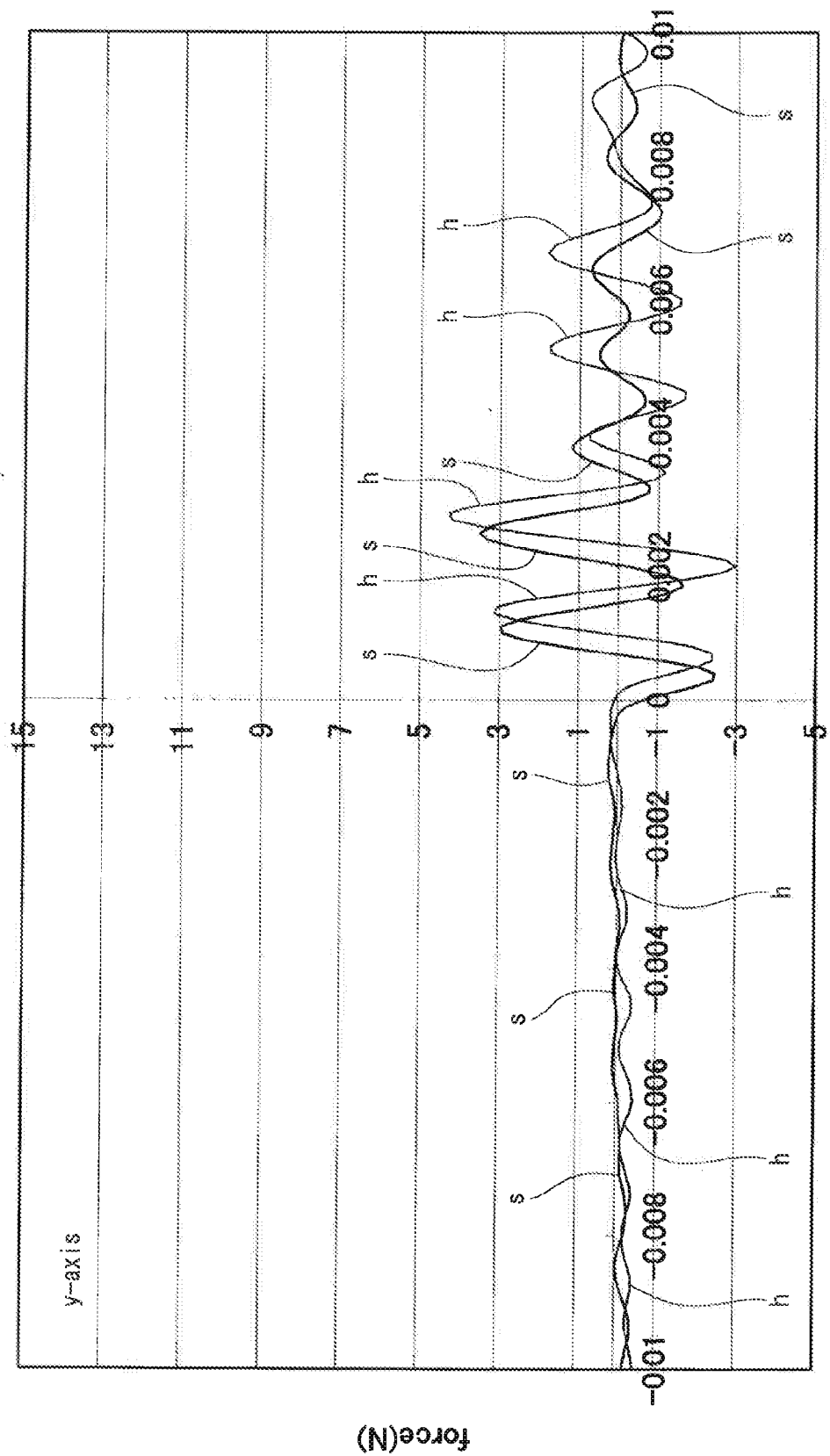
FIG. 27 is a graph showing force in an axis y direction.
Figure 28:
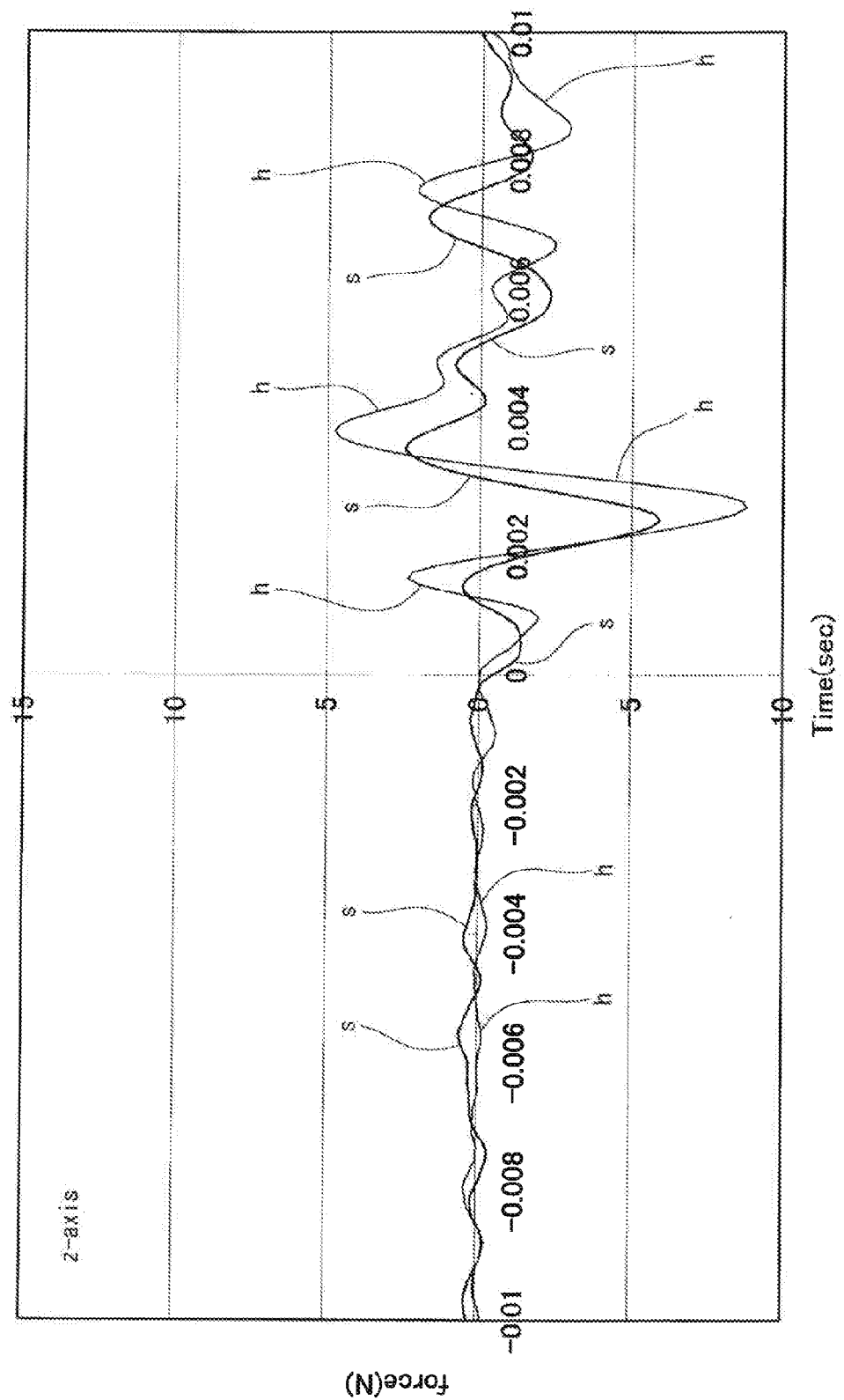
FIG. 28 is a graph showing force in an axis z direction.

FIG. 26 is a graph plotting the result of measurement using the hail Sf and the result of measurement using the ball Hd. FIG. 26 shows the force Fx. FIG. 27 is a graph plotting the result of measurement using the ball Sf and the result of measurement using the ball Hd. FIG. 27 shows the force Fy. FIG. 28 is a graph plotting the result of measurement using the ball Sf and the result of measurement using the ball Hd. FIG. 28 shows the force Fz. In FIG. 26, FIG. 27, and FIG. 28, the symbol a is a graph of the ball Sf, and the symbol h is a graph of the ball Hd.

As shown in FIG. 26, the force Ex when the ball Sf was used and the force Fx when the ball Hd was used are different. As shown in FIG. 27, the force Fy when the ball Sf was used and the force Fy when the ball Hd was used are different. As shown in FIG. 28, the force Fz when the ball Sf was used and the force Fs when the hall Hd was used are different.

Table 1 shown below shows the specifications and the evaluation results of the golf balls.

TABLE 1

Specifications and evaluation results of balls

|  |  |  | Ball X | Commercially Available Item B (Ball B) | Ball Y |
|---|---|---|---|---|---|
| Ball | SCH | Average | 2.35 | 2.20 | 2.35 |
|  |  | σ | 0.022 | 0.040 | 0.017 |
|  | Weight (g) | Average | 45.577 | 45.368 | 45.490 |
|  |  | σ | 0.112 | 0.052 | 0.088 |
|  | Diameter (inch) | Average | 1.6861 | 1.6830 | 1.6841 |
|  |  | σ | 0.0016 | 0.0004 | 0.0011 |
| Cover | Thickness |  | 0.5 | 1.05 | 0.4 |
|  | Material Hardness (D) |  | 32 | 49 | 38 |
| Intermediate Layer | Thickness |  | 1.0 | 1.2 | 1.0 |
|  | Material Hardness (D) |  | 65 | 66 | 65 |
| Inner Intermediate Layer | Thickness |  | — | 1.6 | — |
|  | Material Hardness (D) |  | — | 59 | — |

TABLE 1-continued

Specifications and evaluation results of balls

| | | | Ball X | Commercially Available Item B (Ball B) | Ball Y |
|---|---|---|---|---|---|
| Core | SCH | | 2.75 | 3.40 | 2.75 |
| | Distribution of Hardness | Center | 40 | 34 | 40 |
| | | 5 mm | 48 | 41 | 48 |
| | | 10 mm | 48 | 43 | 48 |
| | | 15 mm | 52 | 49 | 52 |
| | | Surface | 59 | 54 | 59 |
| | Structure | | One-layer Core Two-layer Cover | Two-layer Core Two-layer Cover | One-layer Core Three-layer Cover |

(Note)
Twelve balls of each kind were measured.

In Table 1, "SCH" signifies an amount of compressive deformation. The amount of compressive deformation is an amount of deformation when a ball is compressive deformed at a predetermined speed from state in which the ball is applied a predetermined initial, load to state in which it is applied a predetermined final load.

As described above, the hitting ball feeling can differ in each person. The evaluation results (amount of compressive deformation) in Table 1 do not necessarily correlate with the hitting ball feeling. In the embodiments described above, the correlation between the hitting ball feeling and evaluated values is high. Based on the evaluation results, advantages of the present invention are obvious.

Alternatively, measured value at first time Ta and measured value at second time Tb may be used instead of the maximum value Fmax and the minimum value Fmin. In an evaluation method preferred in this case, the first step includes a step of obtaining a first measured value Vf at the time Ta after the impact and a second measured value Vf at time Tb which is later than the time Ta, and the second step includes a step of determining the hit feeling on the basis of a difference between the two measured values Vf.

The method described above may be applied to an evaluation of the hit feeling in any sport hitting tools.

The description is only an example, and various changes may be made in a scope that does not depart from the essence of the invention.

What is claimed is:

1. A method for quantitatively evaluating hit feeling of a sport hitting tool, including:
   a first step, by using measurement means M1 which can measure force F acting between a swing subject and the sport hitting tool or a specific directional component F1 thereof, obtaining measured values Vf of the force F or the force F1 in a specific interval Z12 from time T1 to time T2 after the impact, and
   a second step of evaluating the hit feeling on the basis of the measured values Vf in the specific interval Z12, wherein the hit feeling is evaluated based on:
   an integrated value Sf of the measured values Vf in the specific interval Z12, or
   a change rate Rd of the measured values Vf in the specific interval Z12.

2. The evaluation method according to claim 1, wherein the force F or the force F1 is force Fs containing a component in a shear direction.

3. The evaluation method according to claim 1, wherein the swing subject is a swing robot.

4. The evaluation method according to claim 1, wherein
   in the first step, the measured values Vf in the specific interval Z12 from the time T1 to the time T2 after the impact are obtained chronologically.

5. The evaluation method according to claim 4, wherein the time T1 is the impact time Tp.

6. The evaluation method according to claim 4, wherein the specific interval Z12 is equal to or less than 100 msec.

7. The evaluation method according to claim 4, wherein the time T1 is time Tmin when the measured value Vf reaches the minimum in a predetermined interval.

8. The evaluation method according to claim 7, wherein
   if time when the measured value Vf reaches the maximum between the impact time Tp and time after a lapse of 50 msec from the tie Tp is defined as Tmax,
   the time Tmin is time when the measured value Vf reaches the minimum between the impact time Tp and the time Tmax.

9. The evaluation method according to claim 1, wherein in the first step, measurement data is sorted by considering uniformity of a swing speed and/or uniformity of hit points.

10. The evaluation method according to claim 1, wherein
    the measurement means M1 includes a force sensor provided in at least one of the swing subject or the sport hitting tool, and
    a measurement region by the force sensor is determined based on a comparison of a distribution of the measured values Vf in practice swinging and a distribution of the measured values Vf in actual hitting.

11. The evaluation method according to claim 10, wherein the force sensor is a three-axis force sensor.

12. The evaluation method according to claim 1, further including a selection step of selecting a measurement region, wherein
    in the selection step, a pressure sensor provided in at least one of the swing subject or the sport hitting tool is used, and in the selection step, the measurement region is selected based on a comparison of a distribution of the measured values in the practice swinging with the pressure sensor and a distribution of the measured values in actual hitting with the pressure sensor, and
    in the first step, the force F or the specific directional component F1 thereof is measured in the measurement region selected in the selection step.

13. The evaluation method according to claim 12, wherein in the first step, the force F or the specific directional component F1 is measured by a three-axis force sensor.

* * * * *